United States Patent
Leff et al.

(10) Patent No.: US 12,226,128 B2
(45) Date of Patent: Feb. 18, 2025

(54) DUAL LOCKING POLYAXIAL SCREW HEAD

(71) Applicant: GLOBUS MEDICAL, INC., Audubon, PA (US)

(72) Inventors: David Leff, Philadelphia, PA (US); John LaColla, West Chester, PA (US); David Peretz, Wynnewood, PA (US); Matthew Bechtel, Philadelphia, PA (US); Darren Clutter, Barto, PA (US); Adam Friedrich, Cinnaminson, NJ (US)

(73) Assignee: Globus Medical, Inc., Audubon, PA (US)

( * ) Notice: Subject to any disclaimer, the term of this patent is extended or adjusted under 35 U.S.C. 154(b) by 271 days.

(21) Appl. No.: 17/817,391

(22) Filed: Aug. 4, 2022

(65) Prior Publication Data
US 2023/0024542 A1    Jan. 26, 2023

Related U.S. Application Data

(63) Continuation of application No. 16/707,183, filed on Dec. 9, 2019, now abandoned.

(51) Int. Cl.
*A61B 17/70* (2006.01)
*A61B 17/88* (2006.01)

(52) U.S. Cl.
CPC ...... *A61B 17/7037* (2013.01); *A61B 17/7032* (2013.01)

(58) Field of Classification Search
CPC . A61B 17/56; A61B 17/7032; A61B 17/7035; A61B 17/7037
USPC ........ 606/264–275, 305, 308, 328, 99, 104, 606/86 A
See application file for complete search history.

(56) References Cited

U.S. PATENT DOCUMENTS

| | | | |
|---|---|---|---|
| 5,681,319 A | 10/1997 | Biedermann et al. | |
| 2002/0026193 A1* | 2/2002 | Barker | A61B 17/7037 606/328 |
| 2007/0055241 A1* | 3/2007 | Matthis | A61B 17/7032 606/267 |
| 2012/0143265 A1* | 6/2012 | Biedermann | B23P 11/005 606/328 |
| 2013/0096622 A1* | 4/2013 | Biedermann | A61B 17/70 606/279 |

(Continued)

FOREIGN PATENT DOCUMENTS

| | | |
|---|---|---|
| EP | 1316294 A2 | 6/2003 |
| JP | 2003180707 A | 7/2003 |

(Continued)

*Primary Examiner* — Eduardo C Robert
*Assistant Examiner* — David C Comstock

(57) ABSTRACT

Systems, methods, and devices for securing a spinal rod are provided. A clamp assembly may include a tulip comprising a first opening and a second opening, wherein an inner surface of the first opening comprises threads; a saddle movably disposed within the tulip between the first and second openings, the saddle comprising a first end and a second end, the first end comprising a portion configured to receive a spinal rod, the second end comprising a cavity configured to receive a pedicle screw, the saddle comprising slots configured to receive a rotating tool; and a threaded locking cap disposed in the first opening.

20 Claims, 27 Drawing Sheets

(56) References Cited

U.S. PATENT DOCUMENTS

| | | | |
|---|---|---|---|
| 2014/0081334 A1 | 3/2014 | Jackson et al. | |
| 2014/0094849 A1 | 4/2014 | Spratt et al. | |
| 2014/0214097 A1 | 7/2014 | Jackson et al. | |
| 2017/0079689 A1* | 3/2017 | Prevost | A61B 17/7037 |
| 2018/0263665 A1 | 9/2018 | Yacoub et al. | |
| 2020/0253644 A1* | 8/2020 | Biedermann | A61B 17/8605 |

FOREIGN PATENT DOCUMENTS

| | | | |
|---|---|---|---|
| JP | 2006511252 A | 4/2006 | |
| JP | 2007021206 A | 2/2007 | |
| JP | 2007513744 A | 5/2007 | |
| JP | 2009511126 A | 3/2009 | |
| JP | 2015536695 A | 12/2015 | |
| JP | 2019198654 A | 11/2019 | |

* cited by examiner

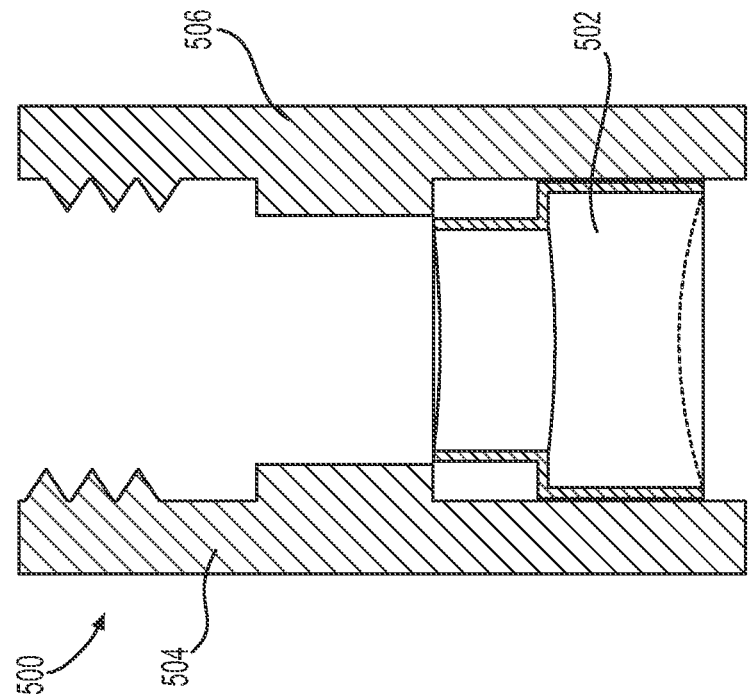
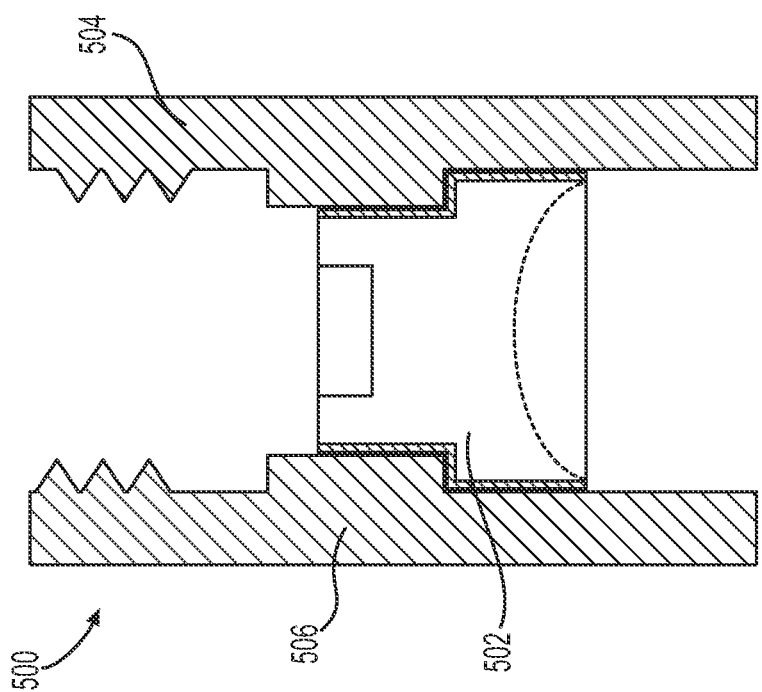
FIG. 5A
FIG. 5B

DUAL LOCKING POLYAXIAL SCREW HEAD

CROSS REFERENCE TO RELATED APPLICATIONS

The present application is a continuation application of U.S. patent application Ser. No. 16/707,183, entitled "Dual Locking Polyaxial Screw Head," filed on Dec. 9, 2019, the entire contents of which are hereby incorporated by reference.

BACKGROUND

Many types of spinal irregularities cause pain, limit range of motion, or injure the nervous system within the spinal column. These irregularities can result from trauma, tumor, disc degeneration, or disease. Typically, these irregularities are treated by immobilizing a portion of the spine. This treatment typically involves affixing a plurality of components, such as, for example, screws, hooks, and/or clamps, to one or more vertebrae, and attaching the components to an elongated rod that stabilizes the vertebrae.

SUMMARY

In an exemplary embodiment, the present disclosure provides a clamp assembly comprising a tulip comprising a first opening and a second opening, wherein an inner surface of the first opening comprises threads; a saddle movably disposed within the tulip between the first and second openings, the saddle comprising a first end and a second end, the first end comprising a portion configured to receive a spinal rod, the second end comprising a cavity configured to receive a pedicle screw, the saddle comprising slots configured to receive a rotating tool; and a threaded locking cap disposed in the first opening.

In another exemplary embodiment, the present disclosure provides a clamp assembly comprising a tulip comprising a first opening and a second opening, wherein an inner surface of the first opening comprises threads; a saddle movably disposed within the tulip between the first and second openings, the saddle comprising a first end and a second end, the first end comprising a portion configured to receive a spinal rod, the second end comprising a cavity configured to receive a pedicle screw, the saddle comprising slots configured to receive a rotating tool; and a threaded locking cap disposed in the first opening.

In another exemplary embodiment, the present disclosure provides a clamp assembly comprising a tulip comprising a first opening and a second opening; a first locking cap removably disposed within the first opening of the tulip; a second locking cap removably disposed within the tulip; a spinal rod extending through the tulip between the first and second locking caps; a pedicle screw; and a saddle movably disposed within the tulip between the second locking cap and a head of the pedicle screw, the head of the pedicle screw disposed within a cavity of the saddle.

In another exemplary embodiment, the present disclosure provides a clamp assembly comprising a tulip, wherein an inner surface of the tulip comprises threads; and a break-off locking cap removably disposed within the tulip. The break-off locking cap may be a threaded locking cap, a set screw, or a quarter turn locking cap.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIG. 5A illustrates a cross-section of a clamp assembly in an initial position in accordance with particular embodiments of the present disclosure;

FIG. 5B illustrates a cross-section of the clamp assembly of FIG. 5A in an actuated position in accordance with particular embodiments of the present disclosure;

DETAILED DESCRIPTION

Figure 1A:
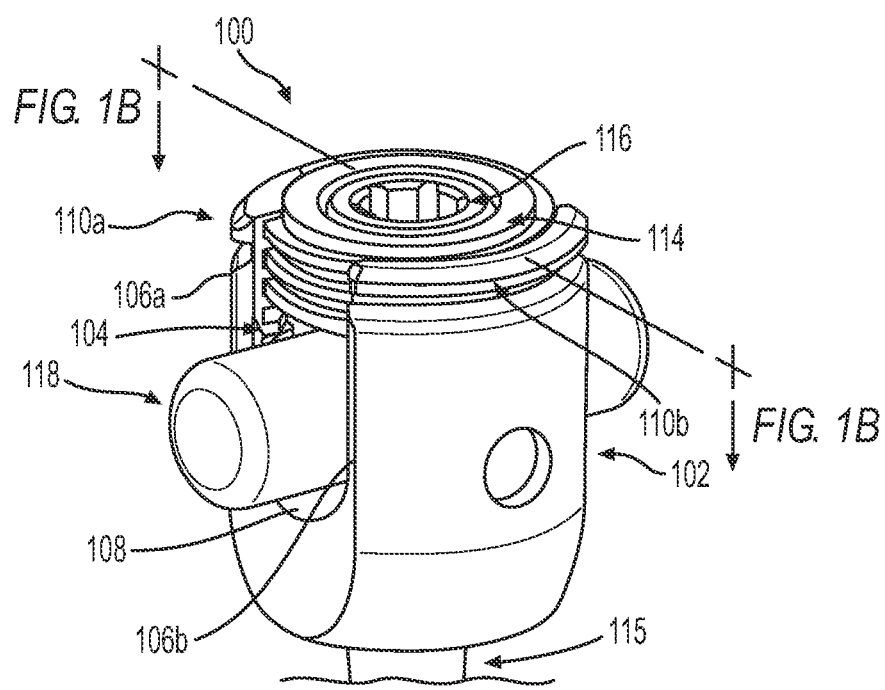
FIG. 1A illustrates a polyaxial clamp assembly ("clamp assembly") 100 in accordance with particular embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments generally relate to spinal surgery. More particularly, embodiments relate to systems, methods, and devices for securing a spinal rod with a polyaxial clamp assembly.

The polyaxial clamp assembly can be utilized for open and percutaneous approaches to the posterior spine. The polyaxial clamp assembly locks or restricts polyaxial motion (e.g., movement in multiple directions) of a screw (e.g., a pedicle screw) before locking or restricting movement of the spinal rod. This allows corrective forces to transfer to vertebra for axial derotation, parallel compression, parallel distraction, and/or reduction.

Although polyaxial motion of the screw may be locked or prevented, the polyaxial screw is free to translate and rotate about the spinal rod. Additionally, the polyaxial motion may also be left unrestricted during correction to allow the same functionality as a typical polyaxial screw. Once correction is achieved, tightening a locking cap into a head of the polyaxial screw secures the spinal rod to prevent movement of the spinal rod.

Particular embodiments of the present disclosure allow restriction of polyaxial motion of a screw head of a pedicle screw, creating a rigid connection between a vertebral body and a surgeon's hand that applies corrective forces. This allows for improved control over motion of the vertebral bodies to aid in correction maneuvers while maintaining the ability of the polyaxial screw to accept a spinal rod at multiple angles. Existing monoaxial screws provide this rigidity but do not accept the spinal rod at multiple angles, requiring accurate contouring of the spinal rod to match a location and orientation of the screw head. Uniplanar screws allow rigidity in one plane but do not accept spinal rods at various angles.

In certain embodiments, spinal rods of varying diameter may be captured and secured by allowing an inner set screw to thread into contact with the spinal rod at varying heights. In particular embodiments, threading an internal locking cap into the spinal rod may compress against a saddle or collet to restrict motion.

FIG. 1A illustrates a polyaxial clamp assembly ("clamp assembly") 100 in accordance with particular embodiments of the present disclosure. The clamp assembly 100 may include a tulip 102. The tulip 102 may be a rigid member that resembles a bullet with a hollow interior. The tulip 102 may include an opening 104 situated between portions 106*a* and 106*b*. A curved portion 108 may be disposed between the portions 106*a* and 106*b*, as shown. The curved portion 108 may be curved to correspond with a shape of a spinal rod 118. In certain embodiments, the opening 104 may extend from the curved portion 108 to distal ends 110*a* and 110*b* of the portions 106*a* and 106*b*, as shown. Inner surfaces 112*a* and 112*b* of the portions 106*a* and 106*b* may be threaded as shown on FIG. 1B. An outer screw 114 may be disposed within the opening 104, as shown. An inner screw 116 may be disposed concentrically within the outer screw 114. The spinal rod 118 may extend through the opening 104, and a screw such as a pedicle screw 115 may extend through a passage 117 (shown on FIG. 1B) of the curved portion 108. In certain embodiments, the spinal rod 118 may extend in a direction that is orthogonal to a longitudinal axis of the concentrically positioned outer screw 114 and inner screw 116.

Figure 1B:
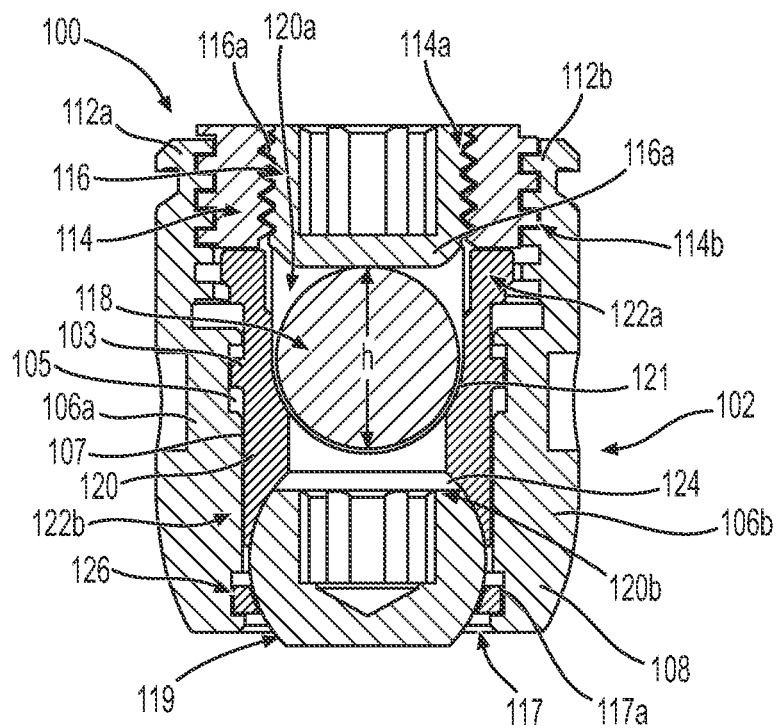
FIG. 1B illustrates a cross section of the clamp assembly 100 in accordance with particular embodiments of the present disclosure.

FIG. 1B illustrates a cross section of the clamp assembly 100 in accordance with particular embodiments of the present disclosure. The cross-section is taken along the dashed line as shown on FIG. 1A. As shown on FIG. 1B, an inner surface 114*a* and an outer surface 114*b* of the outer screw 114 may be threaded. Outer threads 116*a* of inner screw 116 may align or mate with the inner surface 114*a*. The inner surfaces 112*a* and 112*b* of the portions 106*a* and 106*b* may align or mate with the outer surface 114*b*, as shown.

A saddle 120 may be movably disposed within the opening 104, as shown. The saddle 120 may be an elongated rigid member with a shape similar to the tulip 102. The saddle 120 includes an opening 120*a* at a first end 122*a* and an opening 120*b* positioned opposite to the opening 120*a* at a second end 122*b*, as shown. The opening 120*a* may be similar to the opening 104. The saddle 120 may include a ridge 103 that projects into a recess 105 extending along an inner surface 107 of the tulip 102, thereby preventing movement of the saddle 120 beyond the recess 105, as shown.

A screw head 119 of the pedicle screw 115 may be disposed within the passage 117 and the opening 120*b*. The opening 120*b* may include surface topography 124 such as curvature that corresponds with the shape of the screw head 119 to facilitate securing of the pedicle screw 115 within the clamp assembly 100, as shown.

The clamp assembly 100 is permitted to rotate about the screw head 119 via a spherical joint formed between the saddle 120 and screw head 119, as shown. A retaining member 126 is retained in a groove 117*a* of the passage 117 and retains the screw head 119 within the clamp assembly 100 to prevent disassembly, as shown. The retaining member 126 may be a clip or a ring that extends along a circumference of the screw head 119.

In particular embodiments, the spinal rod 118 is accepted by the tulip 102 and then captured by the outer screw 114 which is threaded into the tulip 102 (and may be pre-assembled with the inner screw 116). Further tightening of the outer screw 114 compresses the saddle 120 against the pedicle screw 115, and compresses against the retaining member 126 retained within the tulip 102. This compression restricts the motion of the pedicle screw 115 within the clamp assembly 100 while allowing translation and rotation of the clamp assembly 100 about the spinal rod 118.

Tightening the inner screw 116 secures the spinal rod 118 to the saddle 120, fully restricting all degrees of freedom to form a rigid construct, as shown. The inner screw 116 can be rotated to compress the spinal rod 118 within the opening 120*a*. The spinal rod 118 may be squeezed and secured between an inner surface 121 of the opening 120*a* and a distal end 116*a* of the inner screw 116, as shown.

Figure 2A:
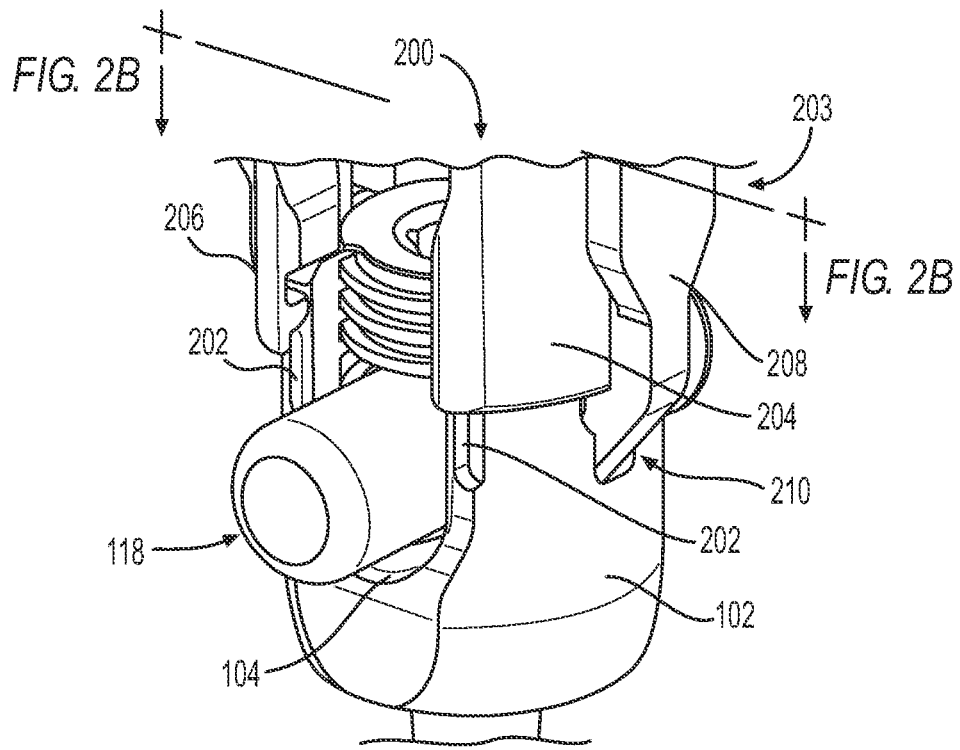
FIG. 2A illustrates a clamp assembly and mating instrument in accordance with particular embodiments of the present disclosure.

FIG. 2A illustrates a clamp assembly 200, in accordance with particular embodiments of the present disclosure. The clamp assembly 200 may be similar to the clamp assembly 100. As shown, the tulip 102 may include grooves 202 extending along a perimeter of the opening 104, as shown. In particular embodiments, the tulip 102 may be movably disposed within a pusher instrument 203 including a sleeve 204 and arms 208, as shown. Rails 206 may extend from the sleeve 204 into the grooves 202 thereby holding and retaining the tulip 102 within the sleeve 204.

Figure 2B:
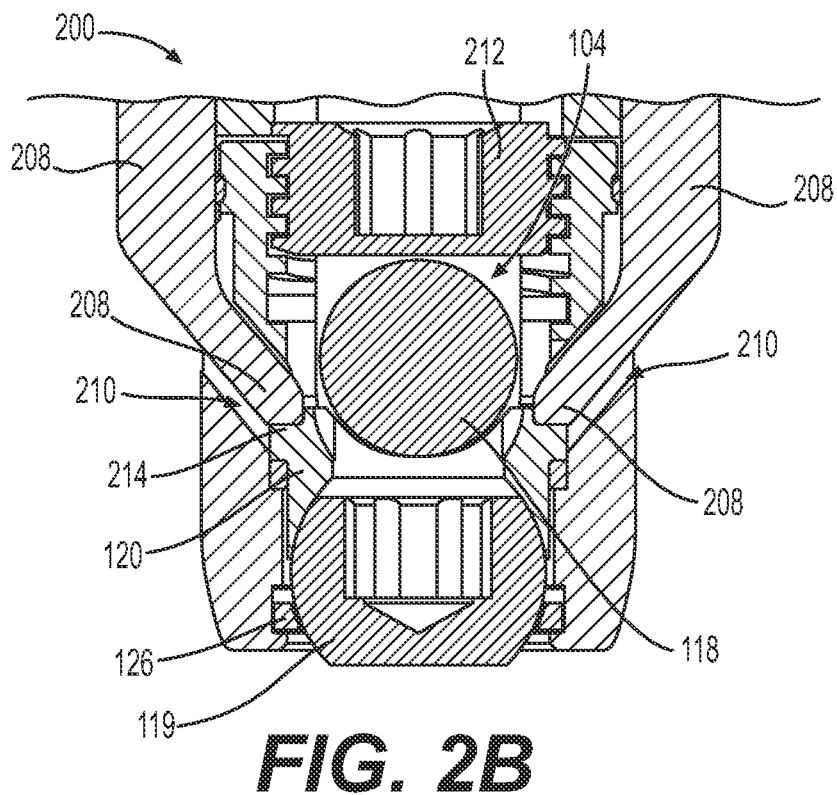
FIG. 2B illustrates a cross section of the clamp assembly and mating instrument of FIG. 2A in accordance with particular embodiments of the present disclosure.

FIG. 2B illustrates a cross section of the clamp assembly 200 in accordance with particular embodiments of the present disclosure. The cross-section is taken along the dashed line as shown on FIG. 2A. As shown on FIG. 2B, the arms 208 may extend from the sleeve 204 into slots 210 of the tulip 102. A locking cap 212 may be disposed within the opening 104 as shown. The locking cap 212 may be similar to the inner screw 116 and/or the outer screw 114. The saddle 120 may include indentations 214 to receive distal ends of the arms 208.

Translation of the pusher instrument 203 compresses the saddle 120 against the screw head 119 which locks or prevents polyaxial motion thereof. As shown, the screw head 119 is compressed between the retaining member 126 and the saddle 120. The spinal rod 118 may then be inserted into the opening 104 before being captured and secured by the locking cap 212, or it may have already been captured by the locking cap 212 before the polyaxial motion was locked. Tightening the locking cap 212 secures the spinal rod 118 to the saddle 120, fully restricting all degrees of freedom to form a rigid construct. The pusher instrument 203 may then be removed.

Figure 3:
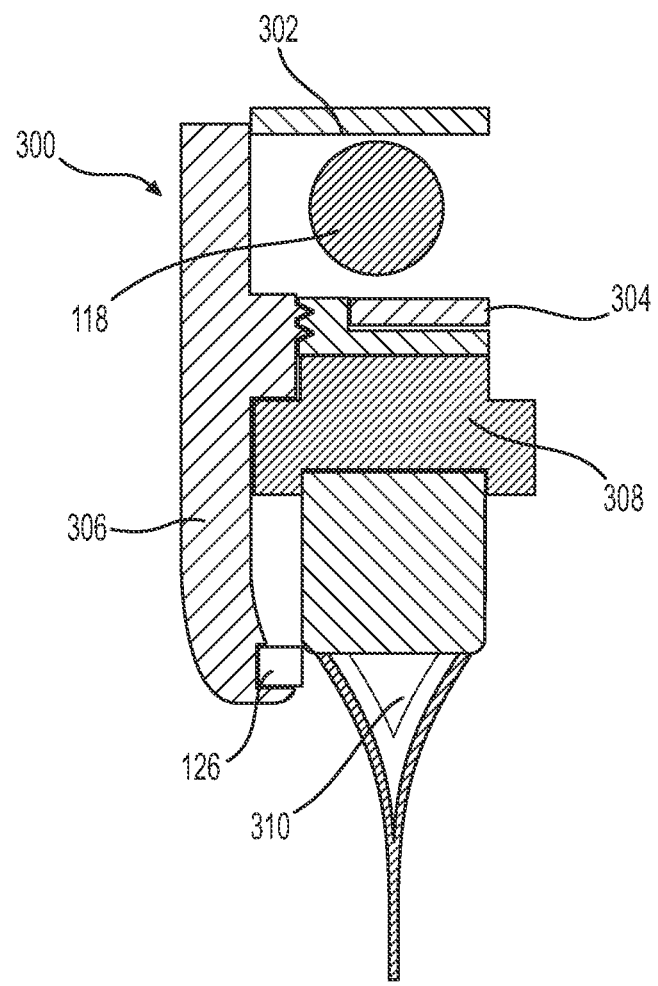
FIG. 3 illustrates a cross-section of a clamp assembly in accordance with particular embodiments of the present disclosure.

FIG. 3 illustrates a cross-section of a clamp assembly 300 in accordance with particular embodiments of the present disclosure. As shown, the clamp assembly 300 includes a first locking cap 302 and a second locking cap 304. Both locking caps 302 and 304 may be threaded into internal threads of the tulip 306. The locking caps 302 and 304 can be rotated to compress a saddle 308 against a screw 310 and the retaining member 126 to lock polyaxial motion, as shown. Then, the spinal rod 118 may be placed to extend between the locking caps 302 and 304, as shown. Not introducing the first locking cap 302 allows the spinal rod 118 to compress against the saddle 308, providing equivalent function as a polyaxial screw. The saddle 308 and first locking cap 302 may be combined into a single component to simplify the design and reduce profile.

Figure 4:
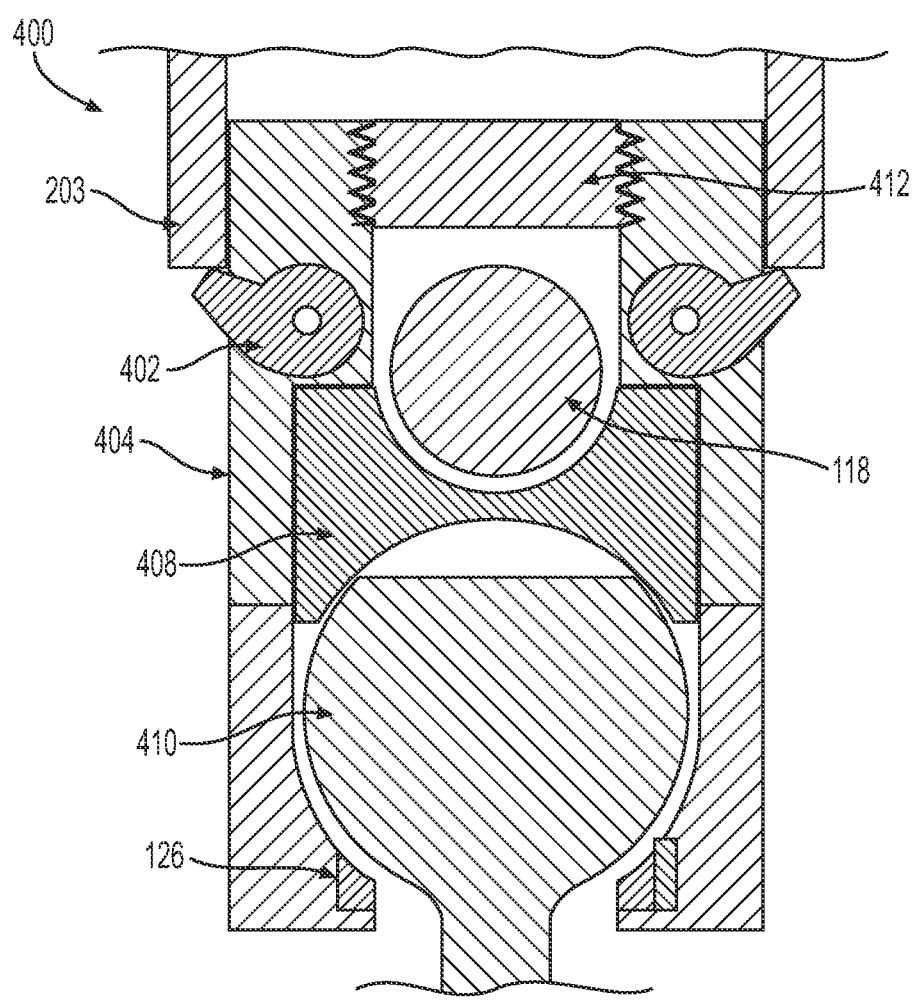
FIG. 4 illustrates a cross-section of a clamp assembly in accordance with particular embodiments of the present disclosure.

FIG. 4 illustrates a cross-section of a clamp assembly 400 in accordance with particular embodiments of the present disclosure. As shown, the clamp assembly 400 includes cam components 402 housed in the tulip 404 are rotated by a pusher instrument component 203 to compress the saddle 408 against the screw 410 and the retaining member 126 to lock the polyaxial motion. The spinal rod 118 may then be introduced and locked against the saddle 408 by the threaded locking cap 412. Compression of the spinal rod 118 against the saddle 408 maintains the polyaxial lock (i.e., restricted movement) after the pusher instrument 203 has been removed.

FIGS. 5A and 5B illustrate cross-sections of a clamp assembly 500 in accordance with particular embodiments of the present disclosure. As shown on FIG. 5A, the saddle 502 is in an initial positioned within the tulip 504. The saddle 502 may be rotated and translates down to compress against a screw (e.g., screw 410 shown on FIG. 4) and a retaining member (e.g., the retaining member 126 shown on FIG. 4).

FIG. 5B illustrates the saddle 502 in an actuated or downward position, as shown. Actuation may occur via an instrument (not shown) which pushes the saddle 502 down, then rotates it under a shelf 506 in the tulip 504. A spinal rod (e.g., the spinal rod 118) may then be introduced and locked against the saddle 502 by a locking cap (e.g., the locking cap 302). Compression of the spinal rod 118 against the saddle 502 maintains the polyaxial lock after the instrument has been removed.

Figure 6:
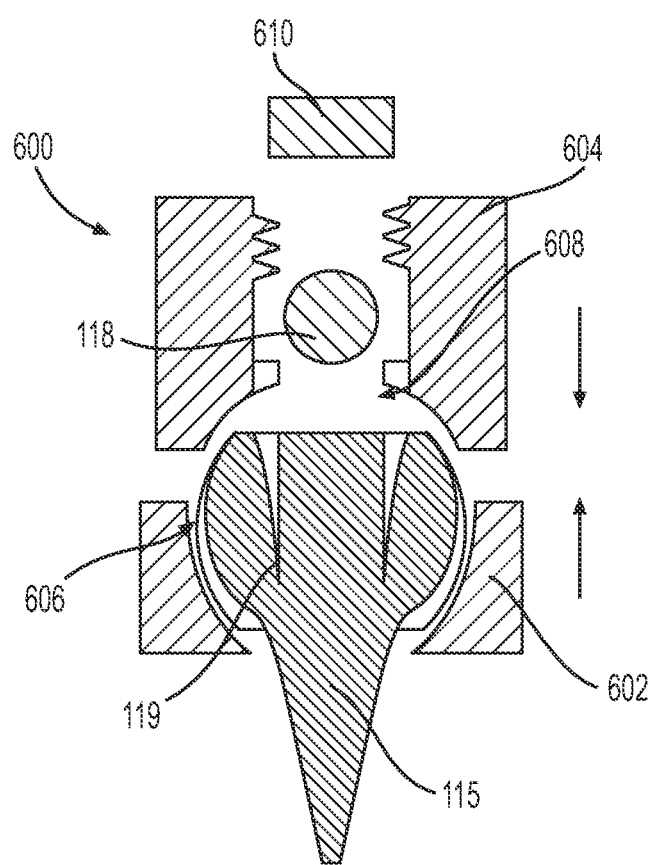
FIG. 6 illustrates a cross section of the clamp assembly in accordance with particular embodiments of the present disclosure.

FIG. 6 illustrates a tulip 600 in accordance with particular embodiments of the present disclosure. As shown, the tulip 600 may be collapsible. A lower portion 602 of the tulip 600 may be separated from an upper portion 604. The lower portion 602 and the upper portion 604 may include or form spherical or conical tapered cavities 606 and 608, respectively, as shown. The shapes of the cavities 606 and 608 may correspond with a shape of the screw head 119 which may be spherical or include a portion that is spherical. The cavities 606 and 608 allow the screw head 119 of the screw 115 to rotate. Translation of the portions 602 and 604 toward each other, as indicated by the arrows, compresses the cavities 606 and 608 around the screw head 119 of the screw 115 to restrict polyaxial motion. This translation may be accomplished by an external threaded nut (not shown). The spinal rod 118 may then be introduced and locked against a saddle (e.g., the saddle 502 as shown on FIGS. 5A and 5B) by a locking cap 610, as shown.

Figure 7:
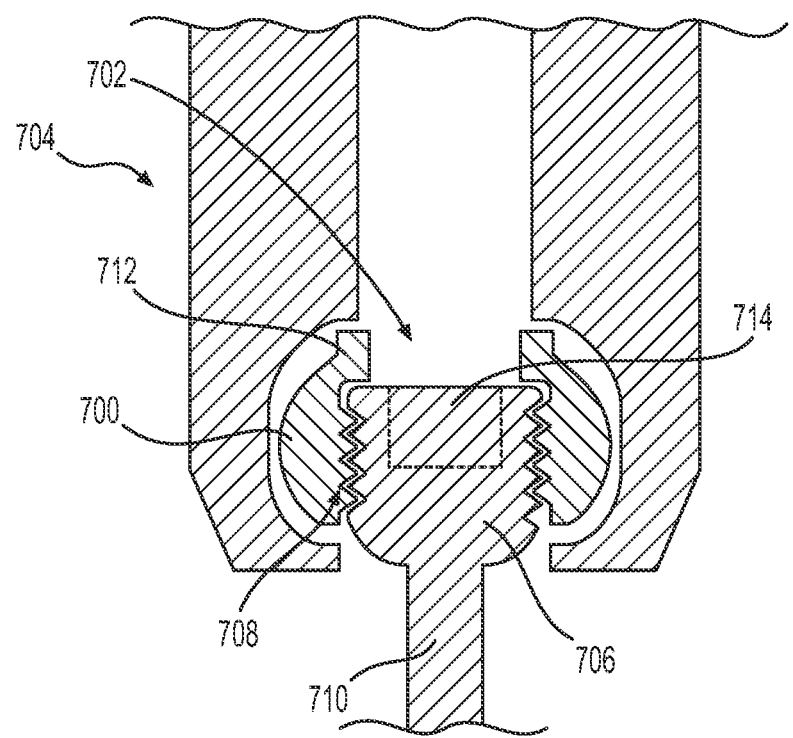
FIG. 7 illustrates a cross section of the clamp assembly in accordance with particular embodiments of the present disclosure.

FIG. 7 illustrates a saddle 700 in accordance with particular embodiments of the present disclosure. The saddle 700 may be a spherical collet or a threaded saddle. As shown, the saddle 700 may be housed in a cavity 702 of a tulip 704 and mates with a threaded screw head 706. The threads 708 between the saddle 700 and threaded screw head 706 are tapered so that when the saddle 700 is rotated with respect to the threaded screw head 706, the saddle 700 expands into the cavity 702, restricting polyaxial motion. A screw 710 may be driven into bone to rotate it with respect to the saddle 700 and the threaded screw head 706. The spinal rod 118 (e.g., shown on FIG. 6) may then be introduced and tightened with the locking cap 610 (e.g., shown on FIG. 6) to compress against the saddle 700 or a saddle component. The retaining member 126 (shown on FIG. 1B) may be disposed in the cavity 702 to allow assembly. In certain embodiments, the saddle 700 may include a driving feature 712 to drive the saddle 700 into position. Also, the screw 710 may include a driving feature 714, as shown.

Figure 8A:
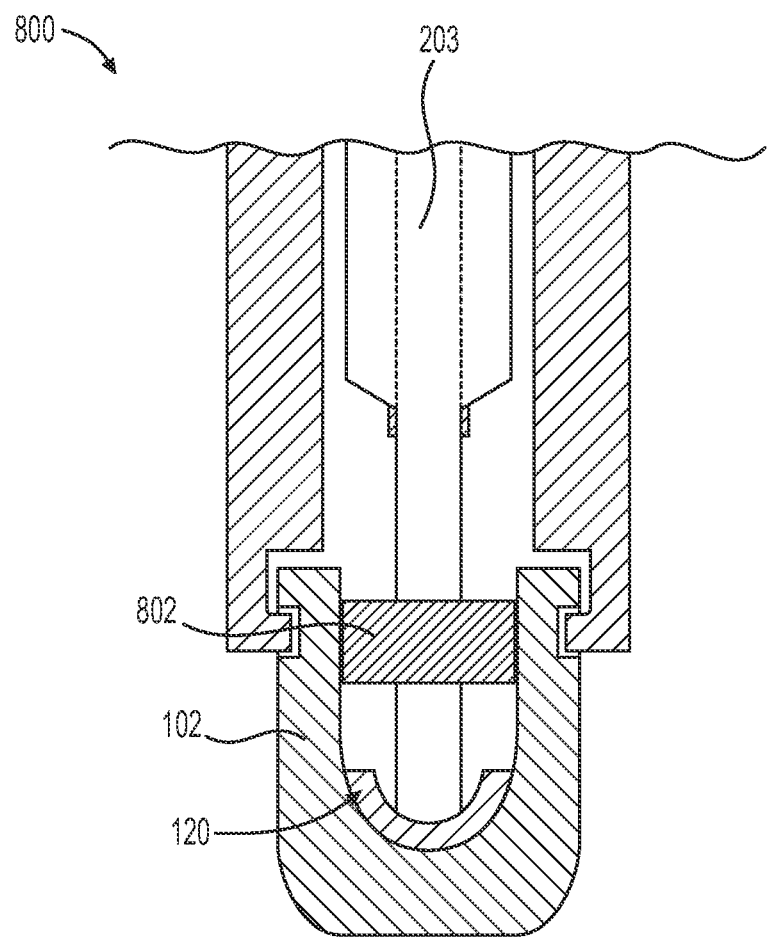
FIG. 8A illustrates a clamp assembly and mating instruments in accordance with particular embodiments of the present disclosure.

FIG. 8A illustrates a clamp assembly 800 in accordance with particular embodiments of the present disclosure. The clamp assembly 800 may be similar to the clamp assembly 200. As shown, the pusher instrument 203 compresses against the saddle 120 to restrict the polyaxial motion. In this embodiment the pusher instrument 203 is inserted through a locking cap 802 to engage the saddle 120 instead of through a side of the tulip 102.

Figure 8B:
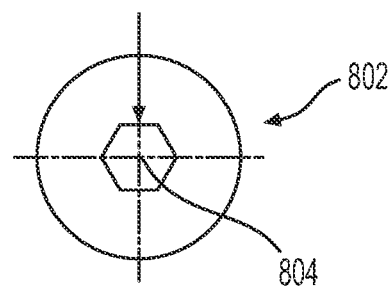
FIG. 8B illustrates a top view of a locking cap of FIG. 8A in accordance with particular embodiments of the present disclosure.

FIG. 8B illustrates a top view of the locking cap 802 in accordance with particular embodiments of the present disclosure. As shown, the locking cap 802 includes a through-hole 804.

Figure 8C:
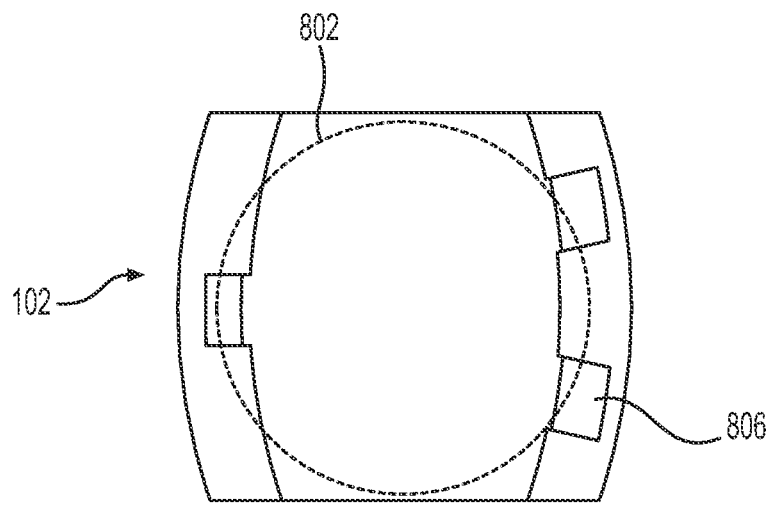
FIG. 8C illustrates a top view of a tulip of FIG. 8A in accordance with particular embodiments of the present disclosure.

FIG. 8C illustrates a top view of the tulip 102 in accordance with particular embodiments of the present disclosure. As shown on FIG. 8C, the tulip 102 includes notches 806 that allow the pusher instrument 203 (e.g., shown on FIGS. 8A and 8D) to be maneuvered around threads 808 (e.g., shown on FIG. 8D) of the tulip 102 to drive the saddle 120 into a locking position.

Figure 8D:
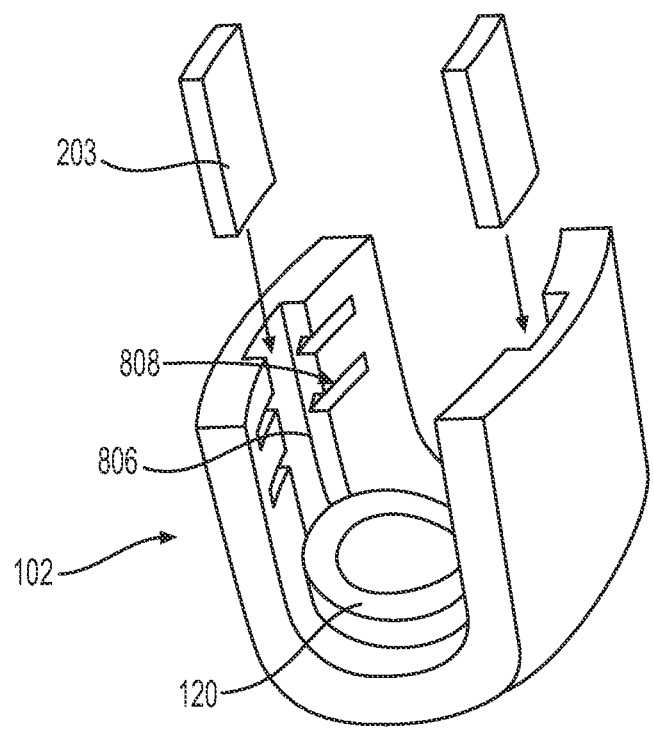
FIG. 8D illustrates a perspective view of the tulip of FIG. 8A in accordance with particular embodiments of the present disclosure.

FIG. 8D illustrates a perspective view of the tulip 102 in accordance with particular embodiments of the present disclosure. As shown, the pusher instrument 203 may be maneuvered through the notches 806 to drive the saddle 120 into a locking position.

Figure 9C:
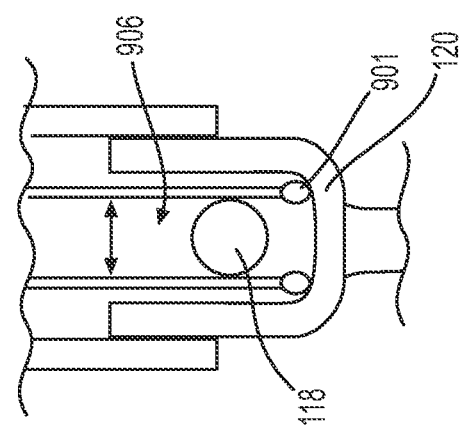
FIG. 9C illustrates a space between the prongs of FIG. 9A in accordance with particular embodiments of the present disclosure.
Figure 9B:
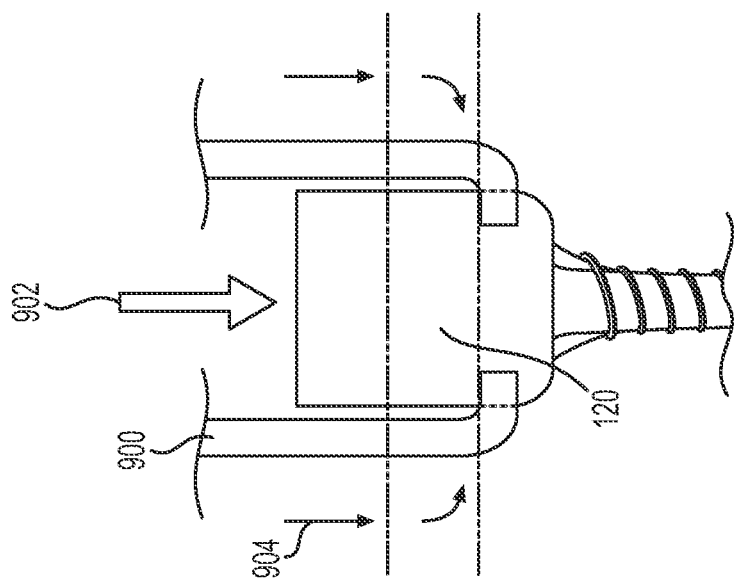
FIG. 9B illustrates the prongs of FIG. 9A contacting a saddle in accordance with particular embodiments of the present disclosure.
Figure 9A:
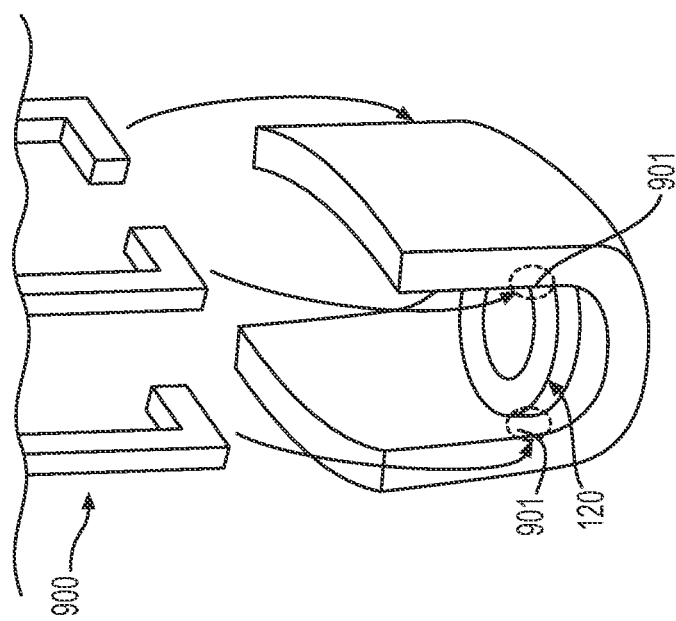
FIG. 9A illustrates prongs utilized to position a saddle in accordance with particular embodiments of the present disclosure.

FIG. 9A illustrates prongs 900 utilized to position the saddle 120 in accordance with particular embodiments of the present disclosure. As shown, the prongs 900 may contact the saddle 120 at corners 901 (e.g., four corners) of the saddle 120.

FIG. 9B illustrates prongs 900 contacting the saddle 120 in accordance with particular embodiments of the present disclosure. A locking cap (e.g., the locking cap 302) may be disposed above the saddle 120 as indicated by arrow 902. As shown, the prongs 900 may reach around the locking cap as indicated by arrows 904.

FIG. 9C illustrates a space 906 between the prongs 900 in accordance with particular embodiments of the present disclosure. The space 906 may be utilized to receive the spinal rod 118. As shown, the prongs 900 may reach around the spinal rod 118 and apply force to the corners 901.

Figure 10A:
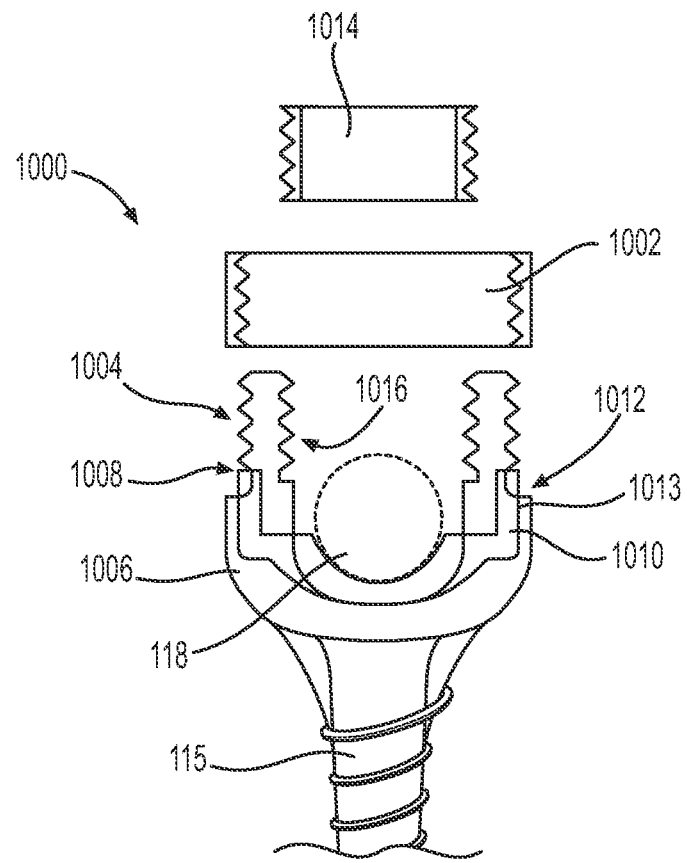
FIG. 10A illustrates a clamp assembly in accordance with particular embodiments of the present disclosure.

FIG. 10A illustrates a clamp assembly 1000 in accordance with particular embodiments of the present disclosure. As shown, an external locking ring 1002 threads onto external threads 1004 of the tulip 1006. Tightening the external locking ring 1002 compresses against extensions 1008 of the saddle 1010 extending through walls 1012 of the tulip 1006 to lock the polyaxial motion of the pedicle screw 115. The extensions 1008 may extend from an external shelf 1013 of the tulip 1006, as shown. Tightening a set screw 1014 to internal threads 1016 of the tulip 1006 locks the spinal rod 118 to the saddle 1010. The external locking ring 1002 may be removed or left on the tulip 1006. The external locking ring 1002 may be an implantable ring or a component of an instrument used to lock motion of the spinal rod 118 and/or the pedicle screw 115.

Figure 10B:
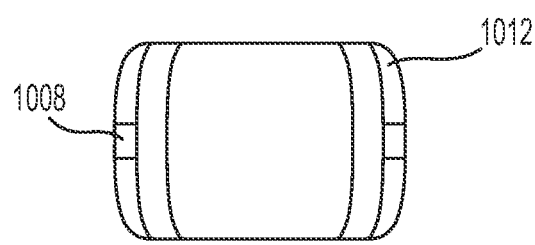
FIG. 10B illustrates a top view of extensions of the clamp assembly of FIG. 10A in accordance with particular embodiments of the present disclosure.

FIG. 10B illustrates a top view of the extensions 1008 in accordance with particular embodiments of the present disclosure. As shown, the extensions 1008 protrude from the walls 1012.

Figure 11A:
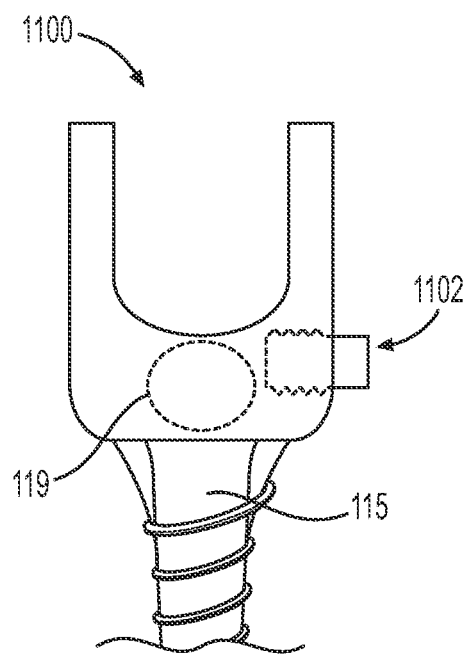
FIG. 11A illustrates a clamp assembly in accordance with particular embodiments of the present disclosure.

FIG. 11A illustrates a clamp assembly 1100 in accordance with particular embodiments of the present disclosure. As shown, a set screw 1102 is tightened to compress against the screw head 119 of the screw 115, restricting polyaxial motion. The set screw 1102 may not be axially aligned with the screw head 119 to allow it to compress the spherical screw head 119, or it may be offset from the screw head 119 with an internal wedge which compresses into the screw head 119 to restrict motion.

Figure 11B:
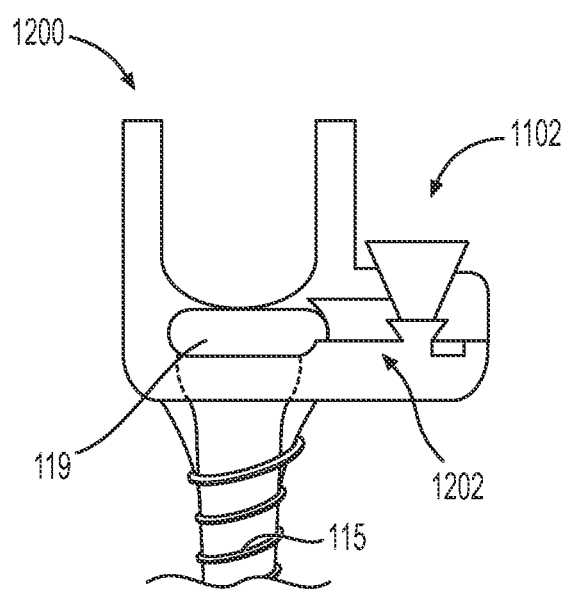
FIG. 11B illustrates a clamp assembly in accordance with particular embodiments of the present disclosure.

FIG. 11B illustrates a clamp assembly 1200 in accordance with particular embodiments of the present disclosure. As shown, the set screw 1102 may contact and drive a wedge 1202 into the screw head 119 of the screw 115 thereby locking the screw 115 in place.

Figure 12:
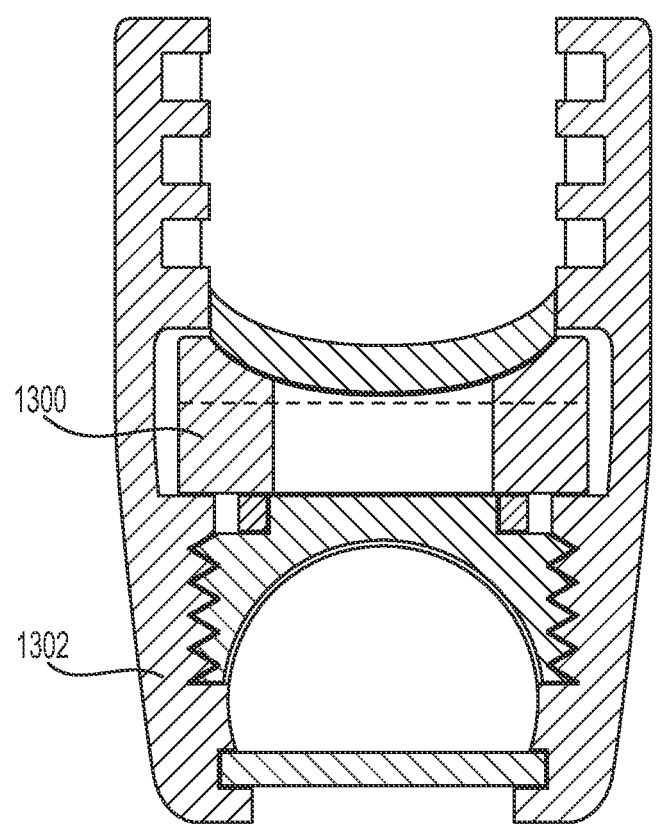
FIG. 12 illustrates a saddle in accordance with particular embodiments of the present disclosure.

FIG. 12 illustrates a saddle 1300 in accordance with particular embodiments of the present disclosure. As shown, a threaded tulip 1302 may be tightened to compress against the spherical head (e.g., screw head 119 of the screw 115 shown on FIG. 11A), restricting polyaxial motion. The threaded tulip 1302 may be combined with the saddle 1300, as shown. The saddle 1300 may be loaded from a top of the threaded tulip 1302 and may be rotated 90° to lock the saddle 1300 in place.

Figure 13:
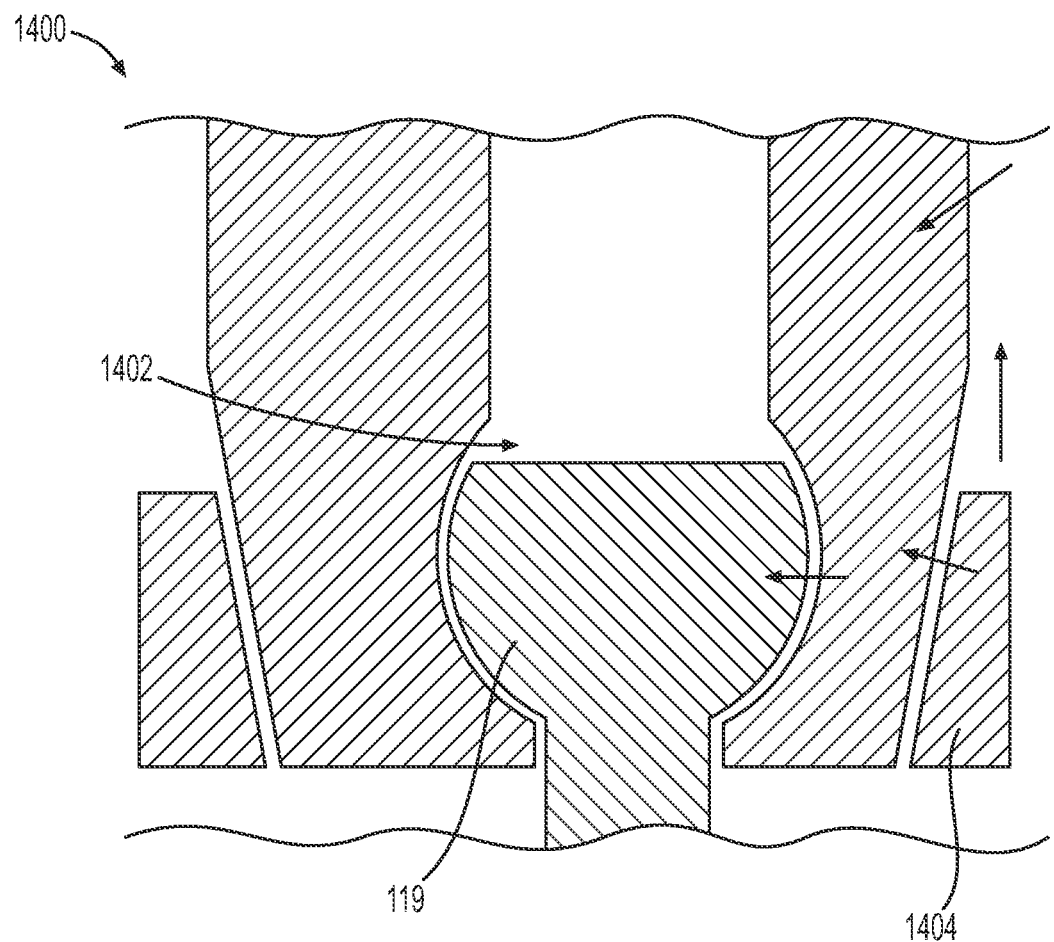
FIG. 13 illustrates a tulip in accordance with particular embodiments of the present disclosure.

FIG. 13 illustrates a tulip 1400 in accordance with particular embodiments of the present disclosure. As shown, the tulip 1300 accepts the screw head 119 in a spherical collet 1402. Translation of an external tapered ring 1404 closes the spherical collet 1402 of the screw head 119 about the screw head 119, restricting polyaxial motion. The external tapered ring 1404 may be translated by an instrument (not shown)

and held in the locked position by a bump feature (not shown) on the screw head 119 or may be threaded onto the screw head 119.

Figure 14B:
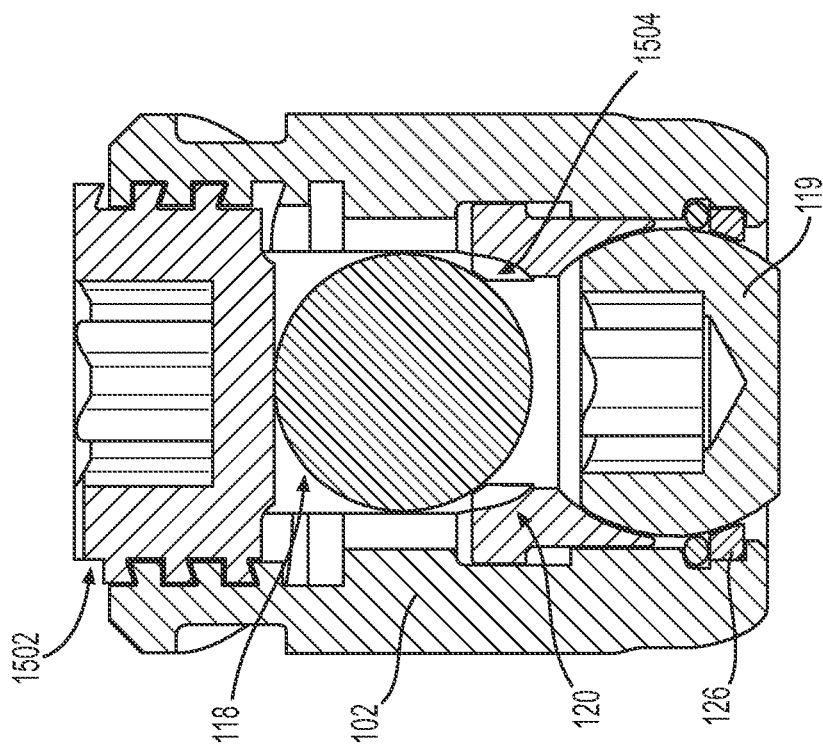
FIG. 14B illustrates a cross-section of the clamp assembly of FIG. 14A in accordance with particular embodiments of the present disclosure.
Figure 14A:
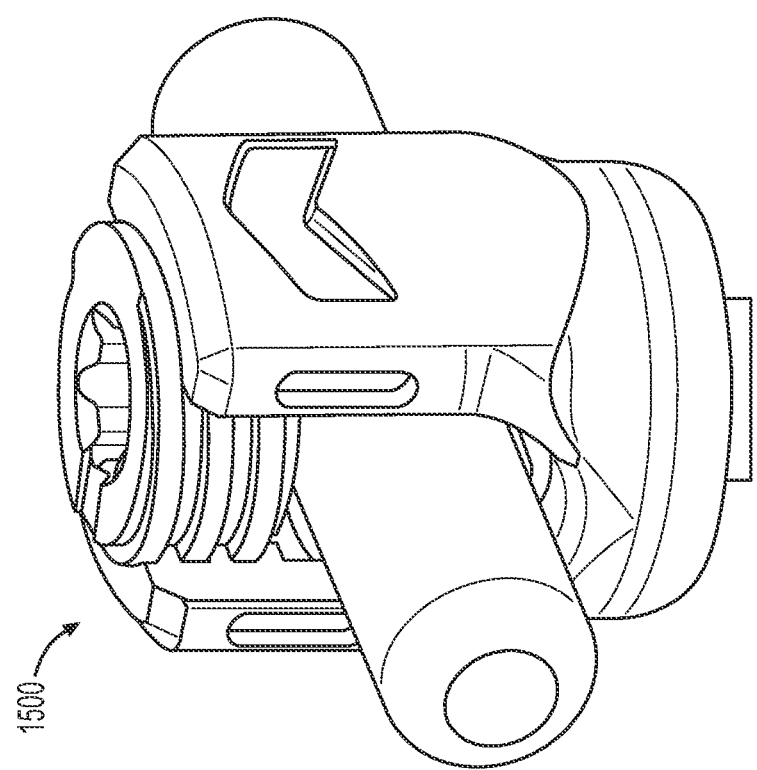
FIG. 14A illustrates a perspective view of a clamp assembly in accordance with particular embodiments of the present disclosure.

FIG. 14A illustrates a perspective view of clamp assembly 1500 in accordance with particular embodiments of the present disclosure. The clamp assembly 1500 may be similar to the clamp assembly 100, as shown on FIG. 1 for example.

FIG. 14B illustrates a cross-section of the clamp assembly 1500 in accordance with particular embodiments of the present disclosure. The clamp assembly 1500 may include a threaded locking cap 1502. The retaining member 126 is retained in the tulip 102 and retains the screw head 119 within the tulip 102 to prevent disassembly. The spinal rod 118 is accepted by the tulip 102 and then captured and secured by the threaded locking cap 1502 which is threaded into the tulip 102, into contact with the spinal rod 118. Further tightening of the locking cap 1502 compresses the spinal rod 118 into a rod slot 1504 of the saddle 120, which compresses the saddle 120 against the screw head 119 and compresses against the retaining member 126 retained within the tulip 102. This compression restricts the motion of the spinal rod 118 and the screw head 119.

Figure 14D:
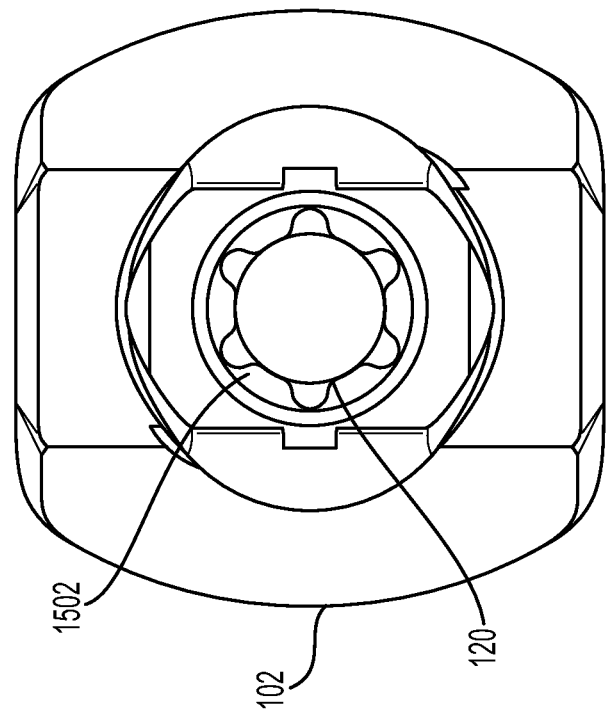
FIG. 14D illustrates a top view of a saddle disposed within a tulip of FIG. 14A, following assembly to a bone screw in accordance with particular embodiments of the present disclosure.
Figure 14C:
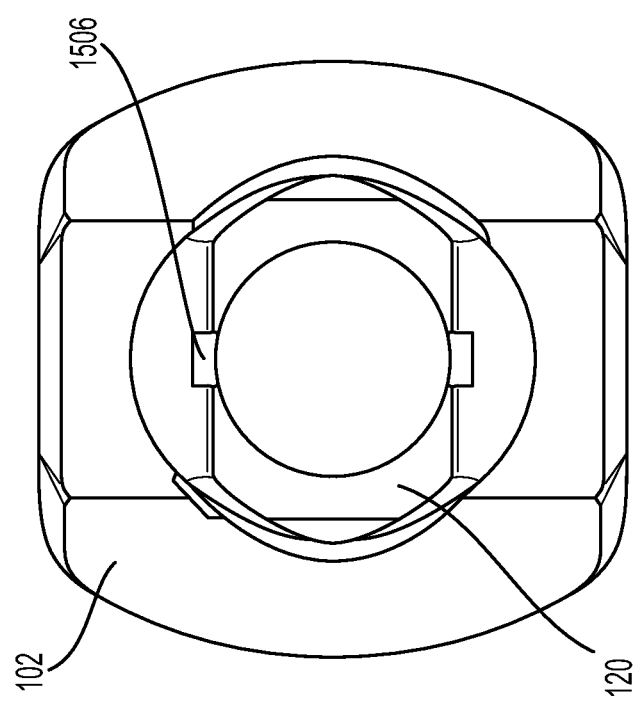
FIG. 14C illustrates a cross-section top view of a saddle disposed within a tulip in accordance with particular embodiments of the present disclosure, prior to assembly to a bone screw.

FIG. 14C illustrates a top view of the saddle 120 disposed within the tulip 102 in accordance with particular embodiments of the present disclosure. The clamp assembly 1500 may be assembled by inserting the saddle 120 into the top of the tulip 102, inserting a screw head 119 into the bottom of the tulip 102, inserting the retaining member 126, then rotating the saddle 120 so that an elliptical profile of the saddle 120 aligns with an elliptical bore of the tulip 102 and prevents the saddle 120 from rotating out of alignment. Slots 1506 cut into the saddle 120 interface with an assembly tool (not shown) to facilitate this rotation.

FIG. 14D illustrates a top view of the threaded locking cap 1502 and the saddle 120 disposed within the tulip 102 in accordance with particular embodiments of the present disclosure. As shown, the threaded locking cap 1502 may be tightened to lock the saddle 120 into place.

Figure 14E:
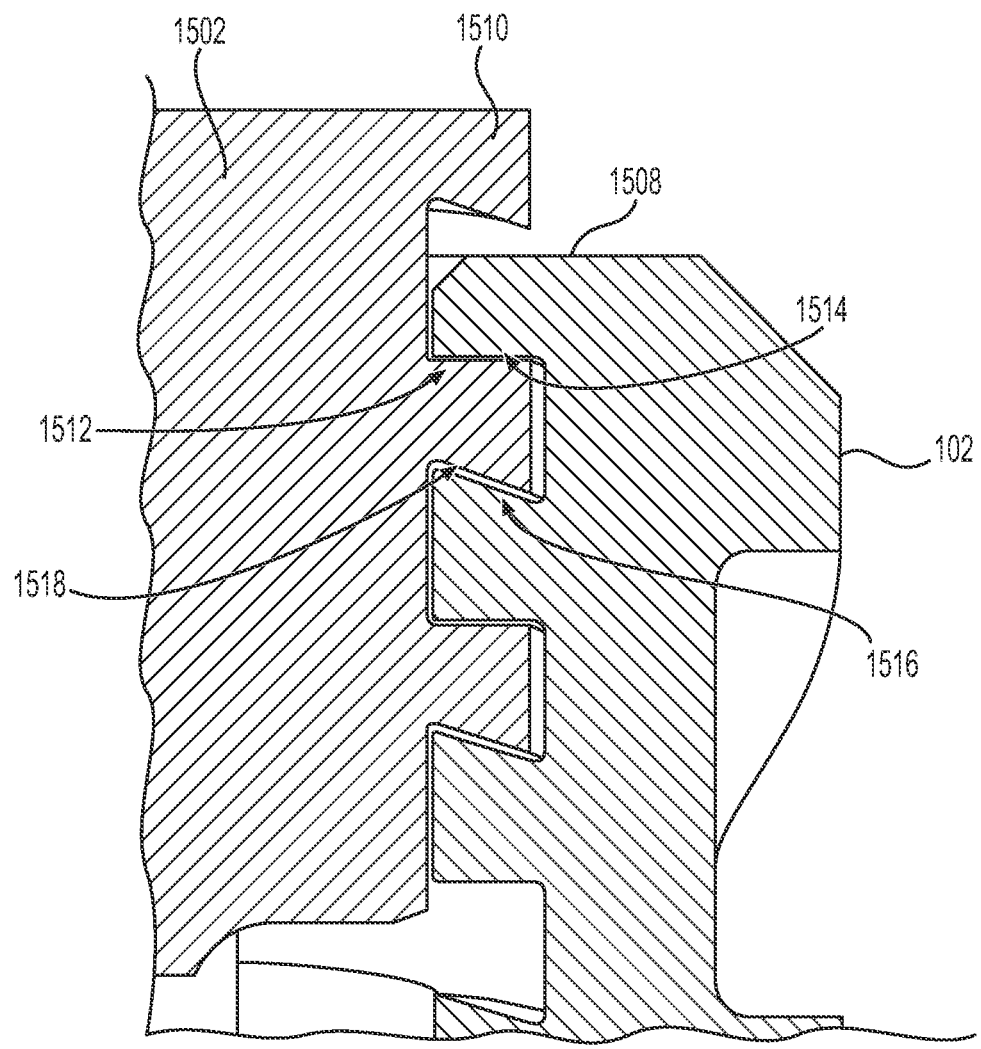
FIG. 14E illustrates a partial cross-section of a tulip of FIG. 14A and the threaded locking cap 1502 in accordance with particular embodiments of the present disclosure.

FIG. 14E illustrates a partial cross-section of the tulip 102 and the threaded locking cap 1502 in accordance with particular embodiments of the present disclosure. As shown, threads 1508 and 1510 include a slight positive angle on upper surfaces 1512 and 1514. The upper surfaces 1512 and 1514 are contacted and loaded when tightened. The lower surfaces 1516 and 1518 of the threads 1508 and 1510 are angled at a greater positive angle than the upper surfaces 1512 and 1514, so that if the screw head 119 were deformed outwards, the lower surfaces 1516 and 1518 should contact and resist the splaying deformation.

Figure 15A:
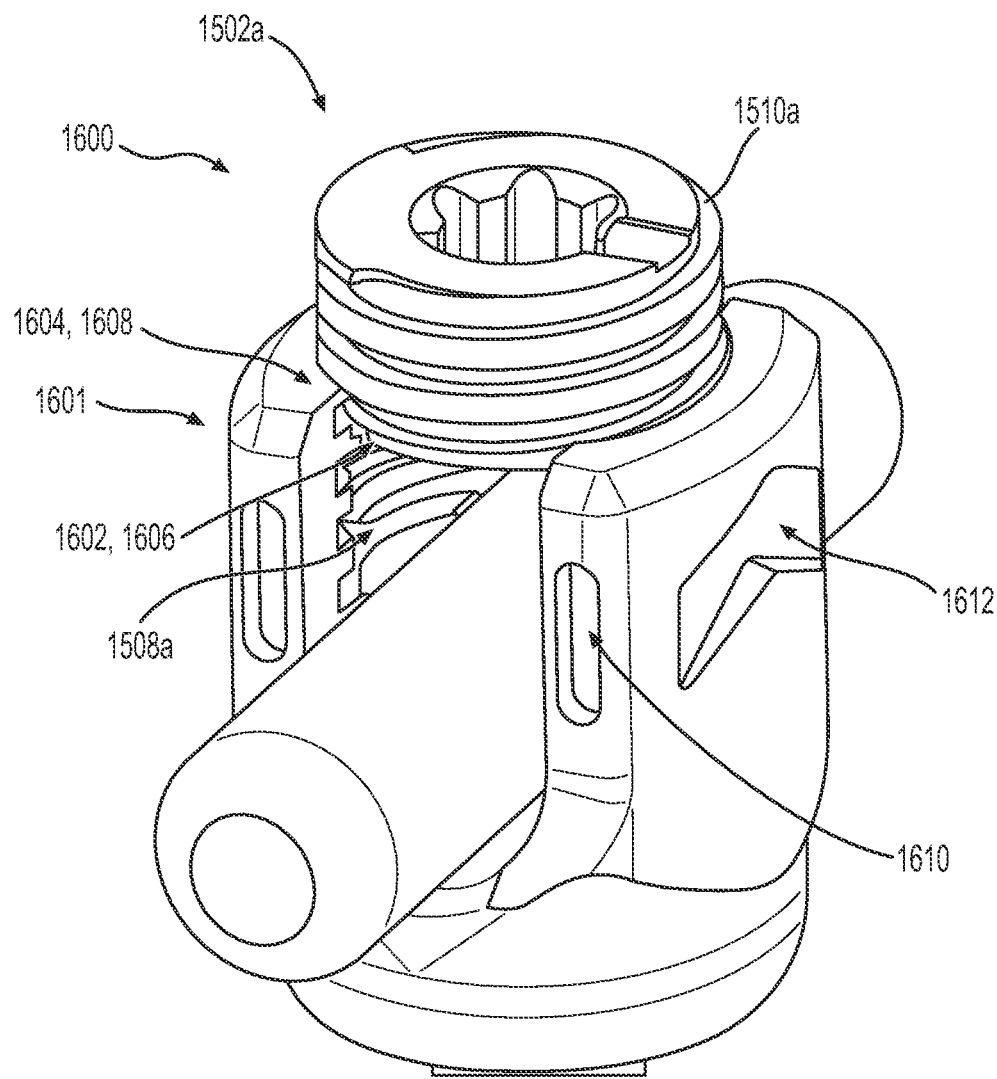
FIG. 15A illustrates a perspective view of a clamp assembly in accordance with particular embodiments of the present disclosure.

FIG. 15A illustrates a perspective view of a clamp assembly 1600 in accordance with particular embodiments of the present disclosure. The clamp assembly 1600 may be similar to the clamp assembly 1500, as shown on FIG. 14A for example. As shown, a bottom portion or start 1602 of the thread 1510*a* in a threaded locking cap 1502*a* and a top portion or start 1604 of the thread 1508*a* of the tulip 1601 are timed with corresponding markings and/or cutouts 1606 and 1608, respectively, in the threaded locking cap 1502*a* and/or the tulip 1601. When the markings and/or cutouts 1606 and 1608 are aligned, the start 1602 is close to engaging the thread 1508*a* of the tulip 1601. This allows the user to quickly and repeatably engage the thread 1510*a* with the thread 1508*a*.

Two sets of instrument interface features on the tulip 1601 allow attachment of instruments for reduction, derotation, and placement. Four obround reduction pockets 1610 or two chevron slots 1612 accept mating obround or "chevron" shaped tabs on instruments (not shown).

Figures 15B, 15C:
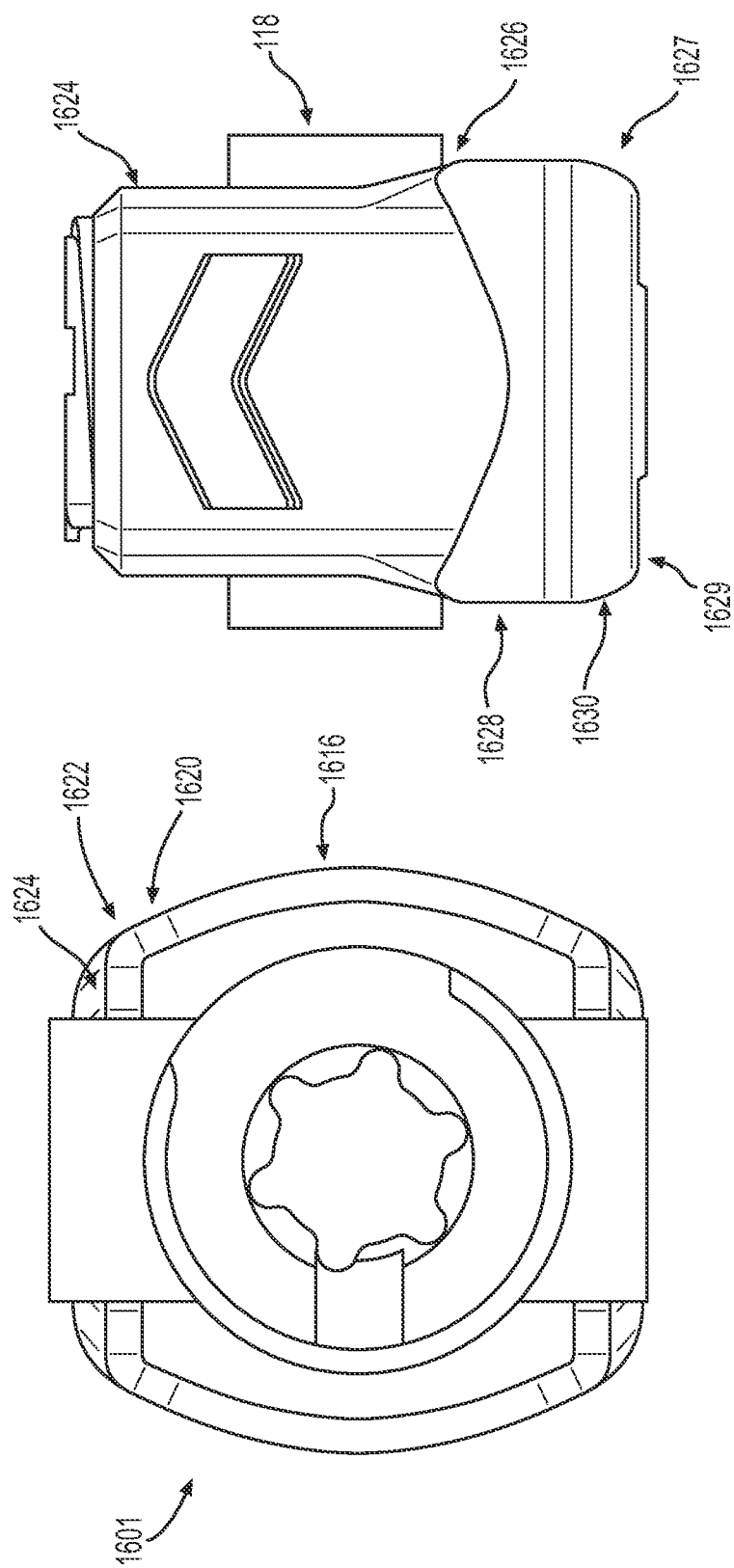
FIG. 15B illustrates a top view of a tulip of the clamp assembly of FIG. 15A in accordance with particular embodiments of the present disclosure.
FIG. 15C illustrates a side view of the clamp assembly of FIG. 15A in accordance with particular embodiments of the present disclosure.

FIG. 15B illustrates a top view of tulip 1601 of the clamp assembly 1600 in accordance with particular embodiments of the present disclosure. As shown, the tulip 1601 includes two large radii 1616, which transition into four angled flat surfaces 1620, which transition into four radii 1622, which transitions into a flat surface 1624 (also shown on FIG. 15C) perpendicular to a rod slot 1626. The spinal rod 118 may extend through the rod slot 1626, as shown.

FIG. 15C illustrates a side view of the clamp assembly 1600 in accordance with particular embodiments of the present disclosure. The lower shape 1627 of the tulip 1601 includes of an outer diameter 1628 which tapers to the lower surface 1629 by a radius 1630, as shown.

Figure 16:
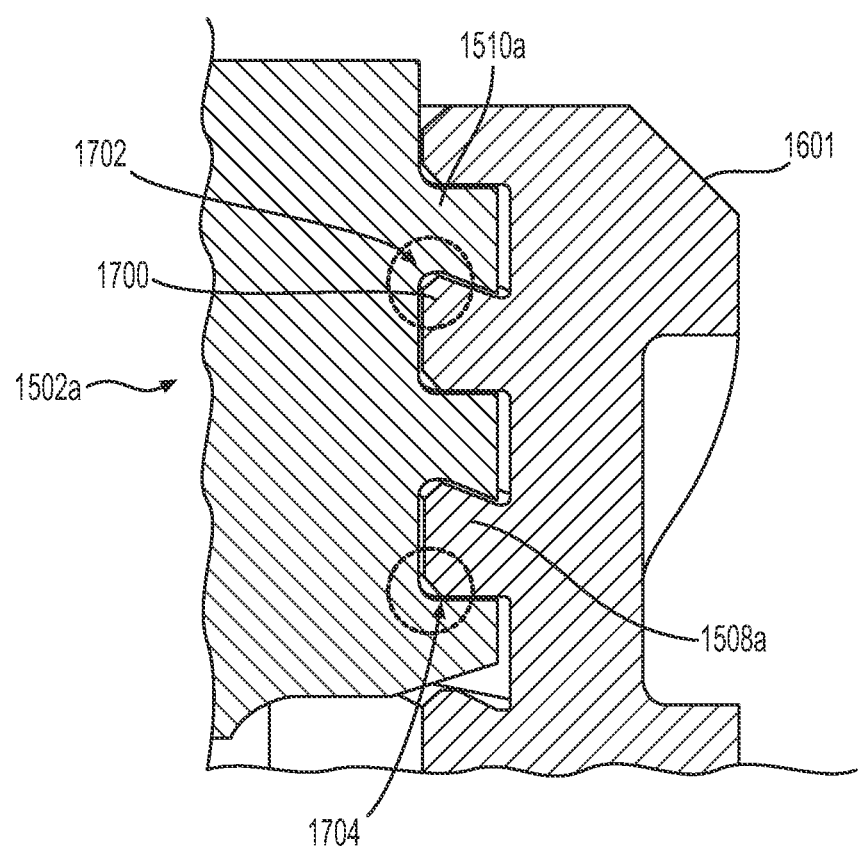
FIG. 16 illustrates a partial cross-section of a tulip and a threaded locking cap in accordance with particular embodiments of the present disclosure.

FIG. 16 illustrates a partial cross-section of the tulip 1601 and the threaded locking cap 1502*a* in accordance with particular embodiments of the present disclosure. As shown, thread 1510*a* includes radii 1700 on inside corners 1702 of the thread 1510*a* to increase strength. Corresponding chamfers or radii 1704 have been added to thread 1508*a* for clearance with the radii 1700.

Figure 17:
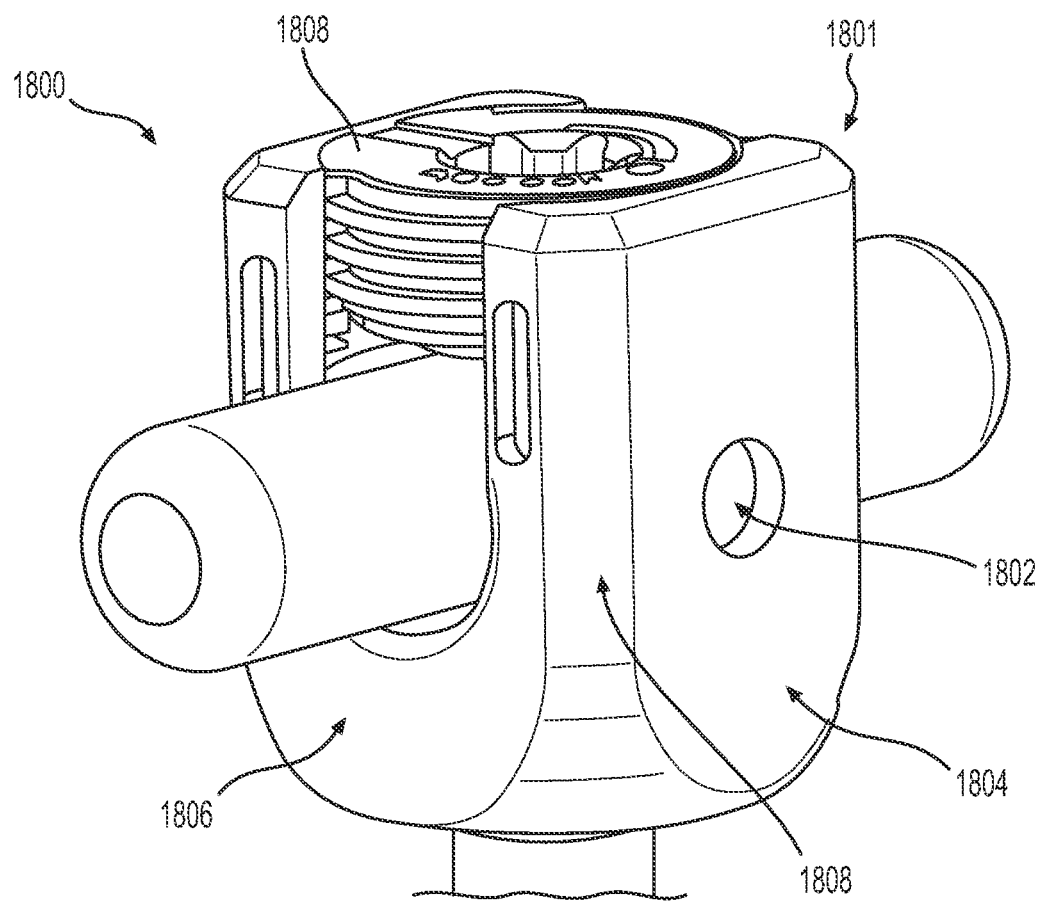
FIG. 17 illustrates a clamp assembly in accordance with particular embodiments of the present disclosure.

FIG. 17 illustrates a clamp assembly 1800 in accordance with particular embodiments of the present disclosure. As shown, the tulip 1801 may include a cylindrical pocket 1802 which interfaces with a corresponding cylindrical feature in a mating instrument (not shown). The tulip 1801 may include perpendicular flat faces 1804 and 1806 cut into a circular diameter 1808. A locking cap 1808 may be threaded into the tulip 1801, as shown.

Figure 18:
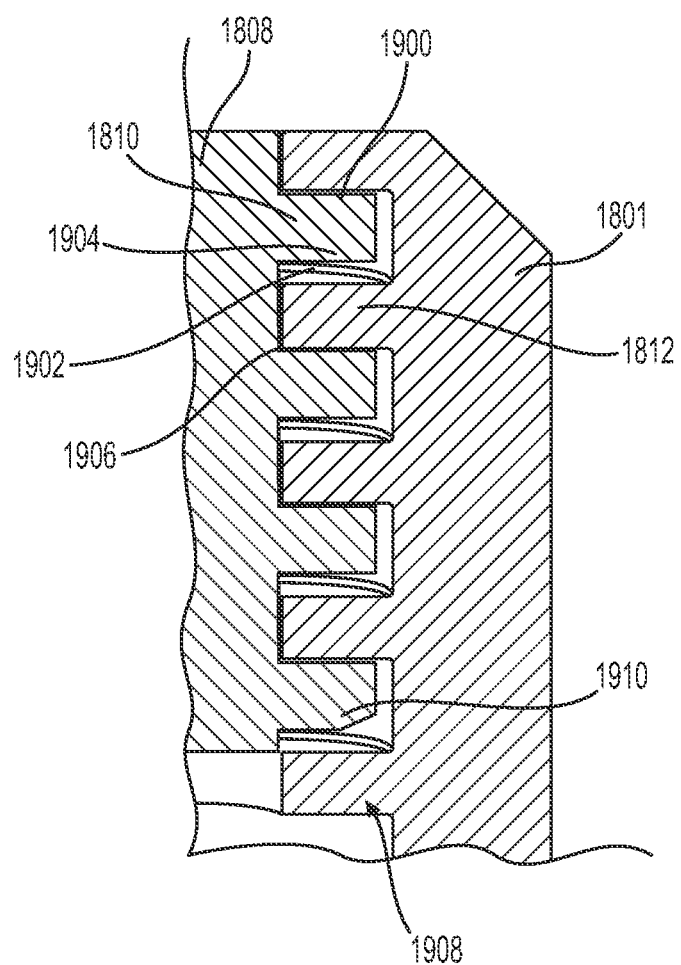
FIG. 18 illustrates a partial cross-section of a tulip and a locking cap in accordance with particular embodiments of the present disclosure.

FIG. 18 illustrates a partial cross-section of the tulip 1801 and the locking cap 1808 in accordance with particular embodiments of the present disclosure. As shown, threads 1810 of the locking cap 1808 and threads 1812 of the tulip 1801 may be square threads. As shown, top surfaces 1900 of threads 1810 and top surfaces 1902 of the threads 1812 and bottom surfaces 1904 (of the threads 1810) and bottom surfaces 1906 (of the thread 1812) are perpendicular to major axis 1908 and minor diameters 1910 of the threads 1810 and 1812, as shown.

Figure 19:
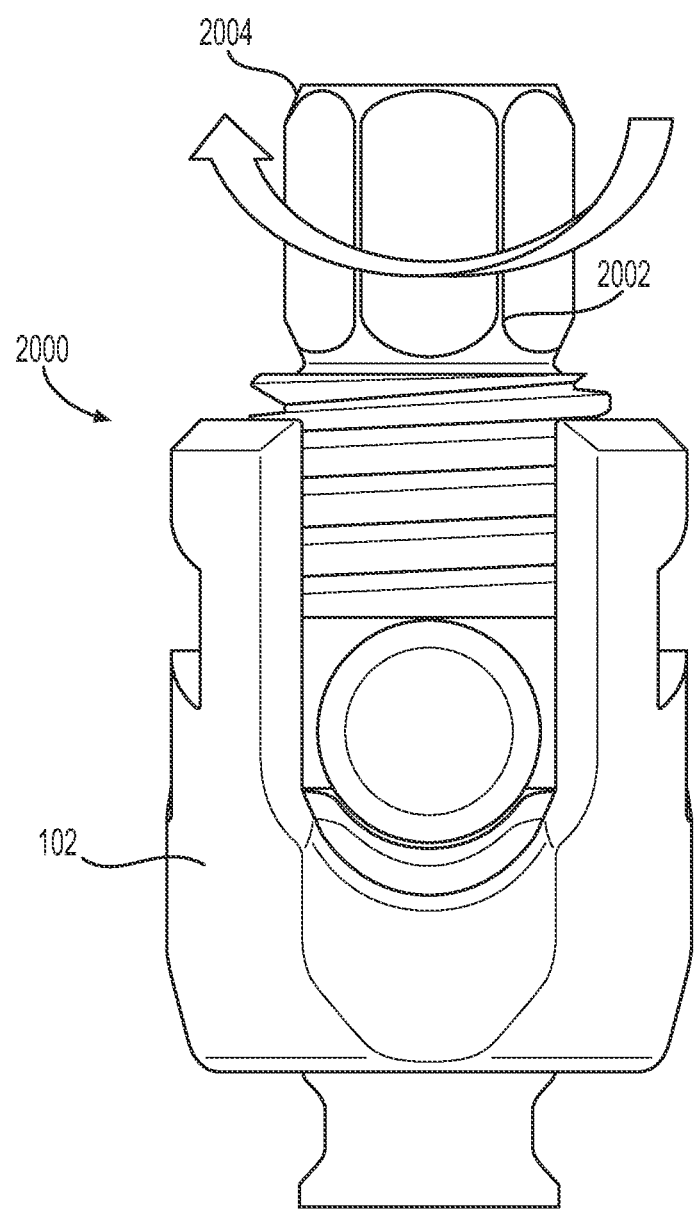
FIG. 19 illustrates a clamp assembly 2000 in accordance with particular embodiments of the present disclosure.

FIG. 19 illustrates a clamp assembly 2000 in accordance with particular embodiments of the present disclosure. As shown, a locking cap 2002 is inserted into or housed within the tulip 102. An instrument (not shown) is used to engage the drive feature (shown on FIGS. 21A and 21B) of the upper portion 2004 of the locking cap 2002 and apply a torque until the point of failure.

A section of the locking cap 2002 is designed to fail at a torque equivalent to the torque required to lock the clamp assembly 2000. This can be done by adding an external or internal groove (see grooves 2004 and 2006 on FIGS. 20A and 20B, respectively) to reduce the cross section of where the break-off feature meets the desired final implant position within the tulip 102, or by pockets or thru holes 2008 (see FIG. 20C) cut to reduce the cross-section.

Figure 20C:
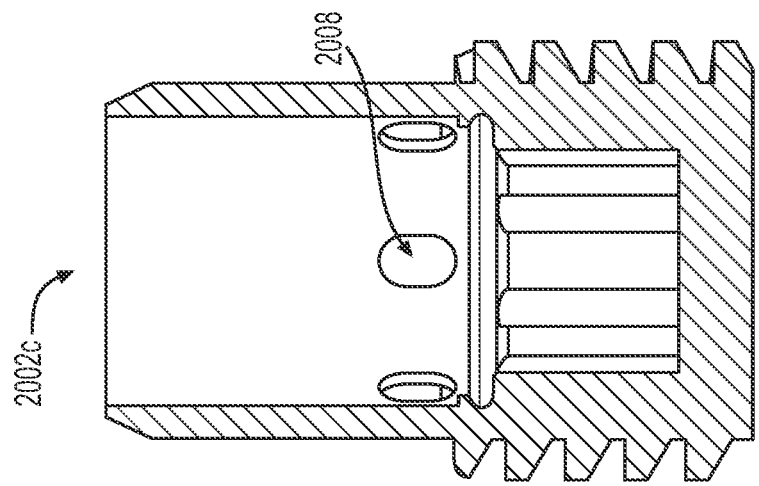
FIG. 20C illustrates a cross-section of a locking cap in accordance with particular embodiments of the present disclosure.
Figure 20B:
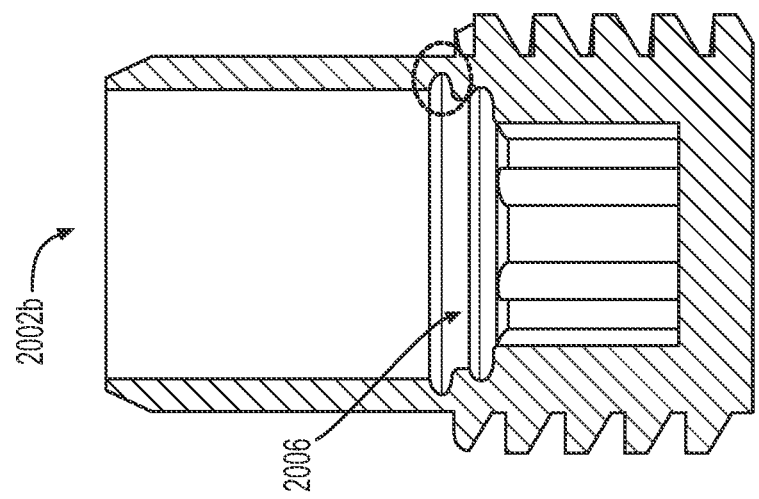
FIG. 20B illustrates a cross-section of a locking cap in accordance with particular embodiments of the present disclosure.
Figure 20A:
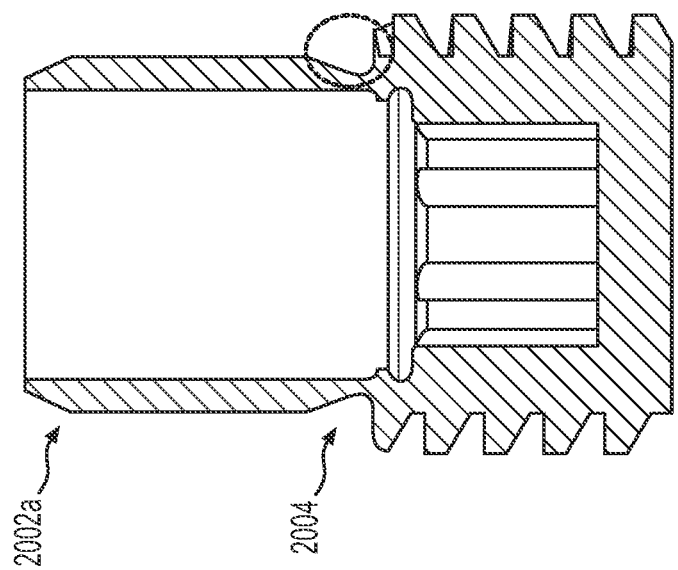
FIG. 20A illustrates a cross-section of a locking cap in accordance with particular embodiments of the present disclosure.

FIG. 20A illustrates a cross-section of a locking cap 2002*a* in accordance with particular embodiments of the present disclosure. As shown, the locking cap 2002*a* may include an external groove 2004 to reduce the cross section of where the break-off feature meets the desired final implant position within the tulip 102.

FIG. 20B illustrates a cross-section of a locking cap 2002*b* in accordance with particular embodiments of the present disclosure. As shown, the locking cap 2002*b* may include an internal groove 2006 to reduce the cross section of where the break-off feature meets the desired final implant position within the tulip 102.

FIG. 20C illustrates a cross-section of a locking cap 2002c in accordance with particular embodiments of the present disclosure. As shown, the locking cap 2002c may include thru holes 2008 to reduce the cross section of where the break-off feature meets the desired final implant position within the tulip 102.

Figure 21B:
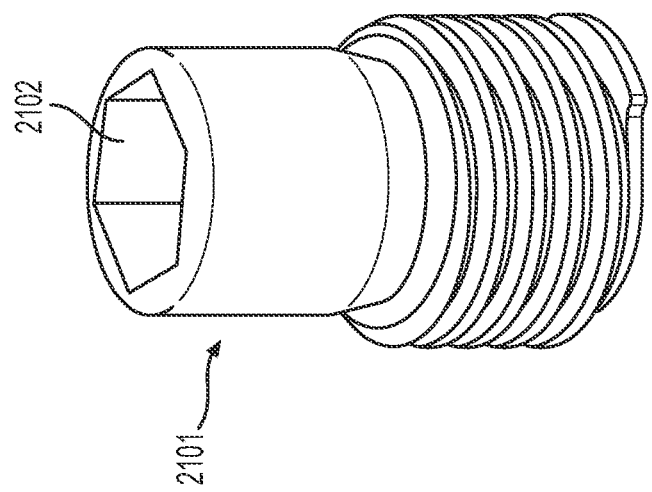
FIG. 21B illustrates a drive feature positioned on a break off portion that is an internal hex drive in accordance with particular embodiments of the present disclosure.
Figure 21A:
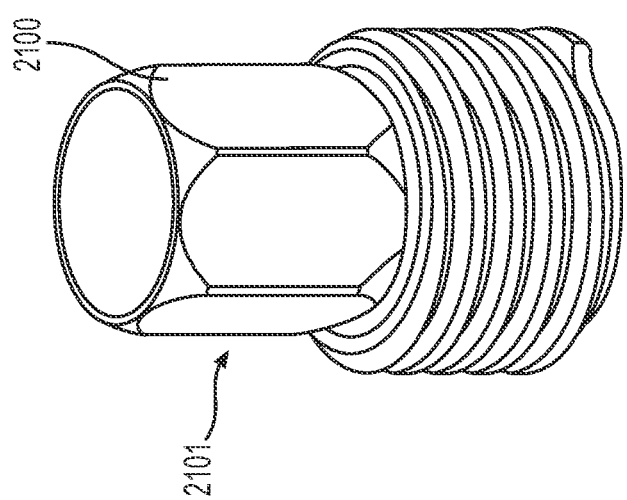
FIG. 21A illustrates a drive feature positioned on a break off portion that is an external hex drive in accordance with particular embodiments of the present disclosure.

FIG. 21A illustrates a drive feature 2100 positioned on a break off portion 2101 that is an external hex drive in accordance with particular embodiments of the present disclosure. FIG. 21B illustrates a drive feature 2102 positioned on a break off portion 2101 that is an internal hex drive in accordance with particular embodiments of the present disclosure. In some embodiments, the drive features 2100 and 2102 may be a hexalobe (torx).

Figure 22:
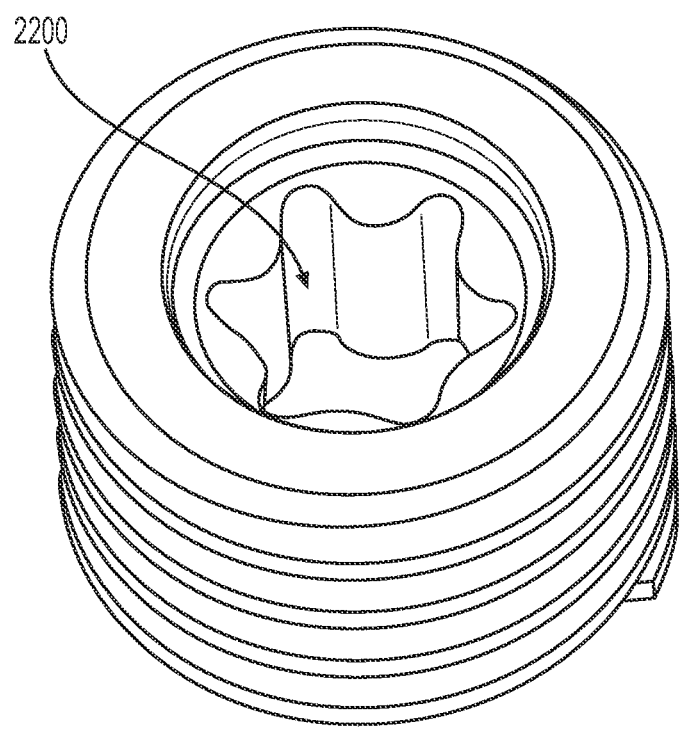
FIG. 22 illustrates a secondary drive feature in accordance with particular embodiments of the present disclosure.

FIG. 22 illustrates a secondary drive feature 2200 in accordance with particular embodiments of the present disclosure. The secondary drive feature 2200 may be left in the tulip 102 to allow for removal or re-tightening.

Figure 23C:
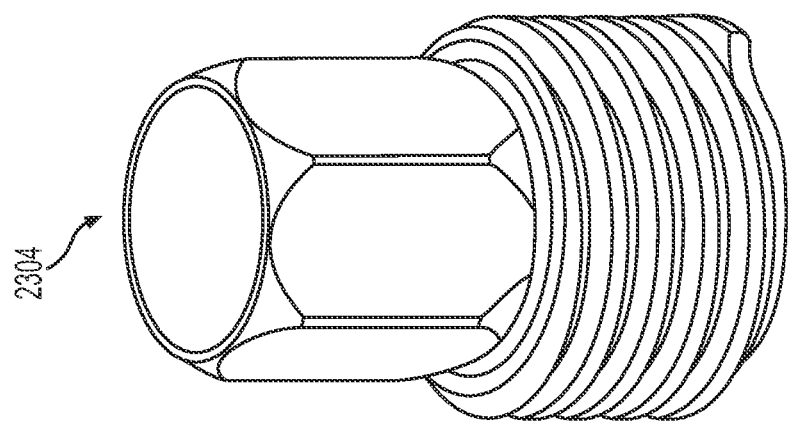
FIG. 23C illustrates a break off feature in accordance with particular embodiments of the present disclosure.
Figure 23B:
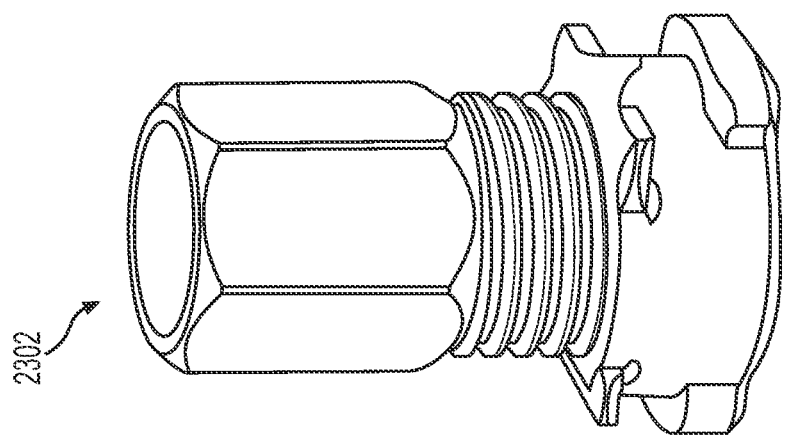
FIG. 23B illustrates a break off feature in accordance with particular embodiments of the present disclosure.
Figure 23A:
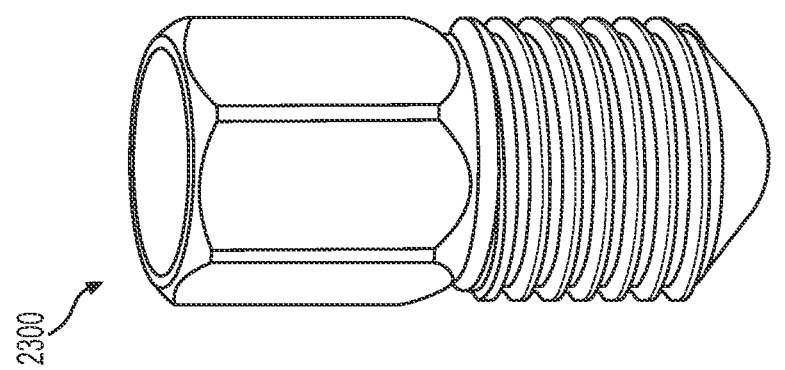
FIG. 23A illustrates a break off feature in accordance with particular embodiments of the present disclosure.

FIG. 23A illustrates a break off feature 2300 in accordance with particular embodiments of the present disclosure. The break off feature 2300 may be a set screw, as shown.

FIG. 23B illustrates a break off feature 2302 in accordance with particular embodiments of the present disclosure. The break off feature 2302 may be a quarter turn locking cap, as shown.

FIG. 23C illustrates a break off feature 2304 in accordance with particular embodiments of the present disclosure. The break off feature 2304 may be a threaded locking cap, as shown.

An advantage of this disclosure is that a consistent torque can be applied upon tightening that does not rely on a torque limiting or torque measuring device which may drift out of calibration and provide an inconsistent torque and is costly and burdensome to recalibrate.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A polyaxial bone screw assembly comprising:
a tulip having a base portion, a first portion extending from the base portion and a second portion extending from the base portion, wherein a first opening is positioned between the first portion and the second portion, wherein a second opening is positioned in the base portion;
a saddle movably disposed within the tulip between the first and second openings, the saddle comprising an upper end and a lower end, the upper end comprising an upper surface configured to receive a spinal rod, the lower end comprising a cavity configured to receive a portion of a screw; and
a screw, the screw having a shaft and a head, wherein the head of the screw is positioned between the saddle and the second opening,
wherein the first portion of the tulip further comprises a first slot for receiving a tool, the first slot extending from an outer surface of the first portion to an inner surface of the first portion,
wherein the saddle includes an indentation on an outer surface of the saddle configured to receive the tool after the tool passes through the outer surface and the inner surface of the first slot.

2. The screw assembly of claim 1, further comprising the spinal rod, the spinal rod extending through the tulip between the first portion and the second portion.

3. The screw assembly of claim 1, wherein at least a portion of the head of the screw is positioned within the cavity.

4. The screw assembly of claim 3, wherein the screw extends through the second opening of the tulip.

5. The screw assembly of claim 1, further comprising a retaining member positioned to abut the head of the screw.

6. The screw assembly of claim 5, wherein the retaining member is positioned proximate the second opening of the tulip.

7. The screw assembly of claim 1, wherein the second portion of the tulip further comprises a second slot for receiving the tool, the second slot extending from an outer surface of the second portion to an inner surface of the second portion.

8. A polyaxial bone screw assembly comprising:
a tulip having a base portion, a first portion extending from the base portion and a second portion extending from the base portion, wherein a first opening is positioned between the first portion and the second portion, wherein a second opening is positioned in the base portion;
a saddle movably disposed within the tulip between the first and second openings, the saddle comprising an upper end and a lower end, the upper end comprising an upper surface configured to receive a spinal rod, the lower end comprising a cavity configured to receive a portion of a screw; and
a locking cap disposed in the first opening,
wherein the first portion of the tulip further comprises a first slot, the first slot extending from an outer surface of the first portion to an inner surface of the first portion, the first slot capable of receiving a pusher tool,
wherein the second portion of the tulip further comprises a second slot, the second slot extending from an outer surface of the second portion to an inner surface of the second portion, the second slot capable of receiving the pusher tool, and
wherein the saddle comprises at least one indentation disposed on an outer surface of the saddle configured to receive the pusher tool after the pusher tool passes through the inner surface of the first slot and inner surface of the second slot.

9. The screw assembly of claim 8, further comprising the spinal rod, the spinal rod extending through the tulip between the first portion and the second portion.

10. The screw assembly of claim 8, further comprising a screw having a head and a shaft, the head of the screw being disposed in the tulip and the shaft extending through the second opening.

11. The screw assembly of claim 10, further comprising a retaining member positioned to abut the head of the screw.

12. The screw assembly of claim 11, wherein the retaining member is positioned proximate the second opening of the tulip.

13. The screw assembly of claim 8, wherein an inner surface of the first opening comprises threads.

14. The screw assembly of claim 13, wherein corners of the threads of the tulip include radii.

15. The screw assembly of claim 13, wherein threads of the tulip are square shaped.

16. The screw assembly of claim 8, wherein the locking cap is threaded.

17. The screw assembly of claim 16, wherein the tulip has threads and the threads of the tulip are angled and wherein the threads of the threaded locking cap are angled.

18. The screw assembly of claim 16, wherein threads of the threaded locking cap are square shaped.

19. The screw assembly of claim 16, wherein the threaded locking cap includes an inner portion disposed concentrically within an outer portion, wherein an outer surface of the inner portion is threaded, wherein an inner surface of the outer portion is threaded.

20. The screw assembly of claim 8, wherein an outer surface of the tulip comprises reduction pockets to receive a mating tool.

* * * * *